US012767723B2

(12) United States Patent
Baltcheva et al.

(10) Patent No.: US 12,767,723 B2
(45) Date of Patent: Oct. 20, 2026

(54) TREATMENT FOR LUPUS NEPHRITIS USING ANTI-BAFFR ANTIBODIES

(71) Applicant: NOVARTIS AG, Basel (CH)

(72) Inventors: Irina Baltcheva, Oberwil (CH); Wolfgang Hueber, Basel (CH); Stephen Oliver, Basel (CH); Olivier Petricoul, Horbourg-Wihr (FR)

(73) Assignee: Novartis AG, Basel (CH)

( * ) Notice: Subject to any disclaimer, the term of this patent is extended or adjusted under 35 U.S.C. 154(b) by 519 days.

(21) Appl. No.: 18/558,730

(22) PCT Filed: May 3, 2022

(86) PCT No.: PCT/IB2022/054056
§ 371 (c)(1),
(2) Date: Nov. 2, 2023

(87) PCT Pub. No.: WO2022/234440
PCT Pub. Date: Nov. 10, 2022

(65) Prior Publication Data

US 2024/0239911 A1 Jul. 18, 2024

Related U.S. Application Data

(60) Provisional application No. 63/184,046, filed on May 4, 2021.

(51) Int. Cl.
*C07K 16/28* (2006.01)
*A61K 9/00* (2006.01)
*A61K 39/00* (2006.01)
*A61P 37/06* (2006.01)

(52) U.S. Cl.
CPC ........ *C07K 16/2878* (2013.01); *A61K 9/0019* (2013.01); *A61P 37/06* (2018.01); *A61K 2039/505* (2013.01); *A61K 2039/545* (2013.01); *C07K 2317/565* (2013.01)

(58) Field of Classification Search
CPC ........................ C07K 16/28; A61K 39/001102
See application file for complete search history.

(56) References Cited

U.S. PATENT DOCUMENTS

| | | | |
|---|---|---|---|
| 2013/0209480 | A1 | 8/2013 | Mpofu et al. |
| 2013/0230538 | A1 | 9/2013 | Kalled et al. |
| 2018/0064828 | A1 | 3/2018 | Chiorini et al. |

FOREIGN PATENT DOCUMENTS

| | | | |
|---|---|---|---|
| CN | 101371923 | A | 2/2009 |
| WO | 2006012508 | A2 | 2/2006 |
| WO | 2006073941 | A2 | 7/2006 |
| WO | 2007142667 | A2 | 12/2007 |
| WO | 2010007082 | A1 | 1/2010 |
| WO | 2013186700 | A1 | 12/2013 |
| WO | 2019136311 | A2 | 7/2019 |
| WO | 2021091706 | A1 | 5/2021 |
| WO | 2022234440 | A1 | 11/2022 |

OTHER PUBLICATIONS

Ding et al (2010), Chin J. Rheumatol., vol. 14, No. 4, pp. 228-232.*
NCT02962895, Novartis Pharmaceuticals Sep. 23, 2021.
Belousov, et al., Clinical Pharmacokinetics. Medication dosing practice, Special Edition, “Rational Pharmacotherapy” Series, 274, 2005.
Corraliza-Gorjon, et al., New Strategies Using Antibody Combinations to Increase Cancer Treatment Effectiveness, Frontiers in Immunology, 8, Dec. 19-20, 2017.
Mashkovsky, Medicines, 16, 2012-1216 (12-13), 2012.
Mould, et al., Pharmacokinetics and Pharmacodynamics of Monoclonal Antibodies, BioDrugs, 24(1), 23-39, 2010.
Oganov, et al., The importance of evidence medicine for clinical practice, Fundamentals of Evidence Medicine, 11, 2010.
Qiao, et al., Agranulocytosis and mixed-type autoimmune hemolytic anemia in primary Sjogren’s syndrome: a case report and review of the literature, International Journal of Rheumatic Diseases, 19(12), 1351-1353, Dec. 2016.
Selezneva, et al., An integrated approach to the study of pharmacological substances in vitro, ex vivo, in vivo, International Scientific Research Journal, 6 (37), 125-127, 2015.
Gueiros, et al., World Workshop on Oral Medicine VII: Immunobiologics forsalivary gland disease in Sjogren’s syndrome: A systematic review, Oral Diseases, 25(1), 102-110, 2019.
Atisha-Fregoso, et al., Phase II Randomized Trial of Rituximab Plus Cyclophosphamide Followed by Belimumab for the Treatment of Lupus Nephritis, Arthritis and Rheumatology, Jan. 2021, 121-131, 73(1).
Blair, et al., Belimumab: A Review in Systemic Lupus Erythematosus, Drugs, Feb. 2, 2018, 355-366, 78(3).
Bowman, et al., Ianalumab (VAY736), a dual mode of action biologic combining BAFF receptor inhibition with B cell depletion, for treatment of primary Sjorgen’s syndrome: results of an international randomized, placebo controlled dose range finding study in 190 patients, ACR/ARP Annual Meeting, Oct. 23, 2019, abstract L19.
Clinical Trial NCT02962895, Nov. 15, 2016, available at https://clinicaltrials.gov/ct2/show/NCT02962895.
Dorner, et al., Ianalumab (VAY736), a dual mode of action biologic combining BAFF receptor inhibition with B cell depletion, reaches primary endpoint for treatment of primary Sjogren’s syndrome, Annals of the Rheumatic Diseases, Jun. 1, 2020, 187-188, 79.

(Continued)

*Primary Examiner* — Prema M Mertz
(74) *Attorney, Agent, or Firm* — David Goetz

(57) ABSTRACT

The present disclosure relates to methods for treating Lupus Nephritis (LN) using an anti-BAFFR antibody or binding fragment thereof, e.g., ianalumab. Also disclosed herein are anti-BAFFR antibodies or binding fragments thereof, e.g., ianalumab, for treating LN patients, as well as medicaments, dosing regimens, pharmaceutical formulations, dosage forms, and kits for use in the disclosed uses and methods.

11 Claims, No Drawings

Specification includes a Sequence Listing.

(56) References Cited

OTHER PUBLICATIONS

Dorner, et al., Treatment of primary Sjorgen's syndrome with ianalumab (VAY736) targeting B cells by BAFF receptor blockade coupled with enhanced, antibody-dependent cellular cytotoxicity, Annals of the Rheumatic Diseases, Mar. 2, 2019, 641-647, 78(5).
Furie, et al., Two-Year, Randomized, Controlled Trial of Belimumab in Lupus Nephritis, The New England Journal Medicine, Sep. 17, 2020, 1117-1128, 383(12).
Schweighoffer, et al., BAFF signaling in health and disease, Current Opinion in Immunology, Aug. 2, 2021, 124-131, 71, WO.
Seror, et al., Current and future therapies for primary Sjögren syndrome, Nature Reviews Rheumatology, Aug. 2021, 475-486, 17.
Wise, et al., Belimumab and Rituximab in Systemic Lupus Erythematosus: A Tale of Two B Cell-Targeting Agents, Frontiers in Medicine, Jun. 30, 2020, article 303, 7.
Zhang, et al., B cell-activating factor and its targeted therapy in autoimmune diseases, Cytokine Growth Factor Reviews, 2022, 57-70, 64.
Clinical Trial NCT02962895, May 30, 2018, available at URL:https://clinicaltrials.gov/study/ NCT02962895.
Doerner, et al., Safety and Efficacy of Single Dose VAY736 (anti-BAFF-RmAb) in Patients with Primary Sjogren's Syndrome (pSS), ACR/ARHP Annual Meeting, 71, 124-131, Sep. 28, 2016.
Escoto, Primary sjogren's syndrome in a child, MOJ Immunology, 6(6), 223-224, Nov. 26, 2018.

* cited by examiner

TREATMENT FOR LUPUS NEPHRITIS USING ANTI-BAFFR ANTIBODIES

SEQUENCE LISTING

The instant application contains a Sequence Listing which has been submitted electronically in ASCII format and is hereby incorporated by reference in its entirety. Said ASCII copy, created on 28 Apr. 2022, is named PAT058081_SL.txt and is 14000 bytes in size.

TECHNICAL FIELD

The present disclosure generally relates to treatments and methods for treating lupus nephritis (LN) using antibody against BAFFR (BAFF receptor), such as ianalumab.

BACKGROUND OF THE DISCLOSURE

LN represents inflammation of the kidneys and is one of the organ-specific disease manifestations of Systemic Lupus Erythematosus (SLE) Lupus 14(1):19-24). LN is a chronic inflammatory disease characterized by auto-antibody production and other distinct immunological abnormalities (Gurevitz et al. (2013) Consult Pharm 28: 110-21). It is categorized histologically into six classes by the International Society of Nephrology/Renal Pathology Society (ISN/RPS) classification system that has become the standard for renal biopsy interpretation because of improved correlation with prognostic and therapeutic outcomes. (Weening et al. (2004) J Am Soc Nephrol. 15(2):241-50; Markowitz et al. (2007) Kidney Int; 71(6):491-5). Immune complex formation in LN is the result of systemic autoimmunity and is a hallmark of the disease (Waldman (2005) Lupus 14(1):19-24; Nowling (2011) Arthritis Res Ther. 13(6):250). Once formed, immune complexes activate complement, which can injure renal cells, leading to either mesangial LN (class I, II), endothelial-proliferative LN (class III, IV), or nephrotic syndrome (class V).

The pathogenesis of LN is complex and involves both the innate and adaptive immune system, various cytokines and tissue, and immune cells. Intra-renal inflammation is maintained via local cytokine and chemokine production and by cells of the innate immune system, such as neutrophils, that are attracted into the glomerulus and interstitium. Targeting local release of pro-inflammatory cytokines by blocking individual cytokines, may enhance treatment efficacy in autoimmunity without increasing systemic immunosuppression. (Allam (2008) Curr Opin Rheumatol; 20(5):538-44; Yu et al. (2017) Nat Rev Nephrol; 13(8):483-95).

Despite recent advances in treatment for several autoimmune diseases, there is still no adequate treatment for LN. It remains a major cause of morbidity and mortality, with 22% of LN patients progressing to ESRD within 15 years (Faurschou et al. (2010) Arthritis Care & Research 62(6): 873-80; Tektonidou et al. (2016) Arthritis Rheumatol. 68(6): 1432-41). There are currently no specific FDA-approved therapies for LN. Current treatments are non-specific, aimed at slowing progression with general immunosuppression. Renal response rates remain suboptimal, underscoring the persistent high unmet need in the treatment of patients with LN.

The American College of Rheumatology (ACR) Guidelines for Screening, Treatment, and Management of Lupus Nephritis have been published in 2012, and are recognized internationally (Hahn et al. (2012) Arthritis Care Res (Hoboken); 64:797-808]. The Joint European League Against Rheumatism/European Renal Association-European Dialysis and Transplant Association (EULAR/ERA-EDTA) guideline has been released the same year (Bertsias et al. (2012) Ann Rheum Dis. 71:1771-82). While there is general agreement of the treatments recommended in these guidelines, these medications have not received either US or European regulatory agency approvals for the indication of LN. It is recommended that LN patients receive several adjunctive medications, such as hydroxychloroquine (HCQ), a lipid-lowering statin and renin-angiotensin-aldosterone system inhibitors (ACE/ARB inhibitors). Where indicated for symptomatic manifestations, steroids are the mainstay of treatment for Class I minimal change LN disease. The ACR guideline does not recommend additional immunosuppression for class II LN. The EULAR/ERA-EDTA guideline recommends low to moderate doses of oral glucocorticoids alone or in combination with azathioprine in cases of proteinuria and hematuria.

The guidelines are uniform in their recommendations for therapy for class III and IV LN and include a sequence of induction and maintenance phases. For patients with class III or IV proliferative glomerulonephritis, the ACR guidelines agree on induction therapy with mycophenolate mofetil (MMF) or i.v. cyclophosphamide (CYC), with or without initial pulses of i.v. methylprednisolone. With current induction regimens, <60% of class III to V patients achieve a complete response (Appel et al. (2009) J Am Soc Nephrol. 20: 1103-1112). Among those who attain a complete renal response (CRR) with current standard-of-care (SoC), nearly half of the patients had a relapse. The rate of relapse in these patients was 5 to 15 per 100 patient-years (Grootscholten et al. (2006) Nephrol Dial Transplant 21:1465-1469).

Patients with class V lupus nephritis are typically treated with antiproteinuric and antihypertensive medications and can receive corticosteroids and immunosuppressive therapy as required depending on the presence of persistent nephrotic proteinuria.

Several histological features affect treatment decisions and prognosis. For example, patients with high "activity" (A) lesions are typically treated with immunosuppression, whereas those with "chronic" (C) lesions may not receive immunosuppressive therapy because of a poorer response prognosis (Hiramatsu et al. (2008) Rheumatology (Oxford) 47:702-07].

Medical treatment of LN with the current SoC achieves a satisfactory renal response only in about half of the patients, and carries a significant burden with respect to safety. Non-responders to the current induction and maintenance therapies have the worst outcomes. Among patients with class IV LN, about 40% developing ESRD at 15 years (Tektonidou et al. (2016) Arthritis Rheumatol. 68(6):1432-41). Thus, despite the aggressive nature of SoC treatment, only up to 40% of patients achieve a CRR after 1 year (Rovin et al. (2014) Am J Kidney Dis. 63(4):677-90). In addition, current LN treatment regimens have substantial side effects from glucocorticoids and prolonged immunosuppression (Schwartz et al. (2014) Curr Opin Rheumatol. 26:502-09). Immunosuppressed LN patients are at significant risk of developing serious infections. In a multiethnic Medicaid cohort, the incidence rate of serious infections was >2-fold higher in LN than SLE patients (Feldman et al. (2015) Arthritis Rheumatol. 67:1577-85).

Given the severity of the condition and the lack of approved therapy, there is a high unmet medical need for safe and effective long-term therapies (i.e., stand alone or as add-on therapies) for the treatment of LN.

Antibodies against BAFFR are known from e.g. WO 2010/007082 and include antibodies which are characterized by comprising a VH domain with the amino acid sequence of SEQ ID NO: 1 and a VL domain with the amino acid sequence of SEQ ID NO: 2. The antibody MOR6654 is one such antibody (IgG1 kappa). It has the heavy chain amino acid sequence of SEQ ID NO: 9 and the light chain amino acid sequence of SEQ ID NO: 10. This antibody may be expressed from SEQ ID NOs: 14 and 15, preferably in a host cell which lacks fucosyl-transferase to provide a functional non-fucosylated anti-BAFFR antibody with enhanced ADCC. This antibody is referred to hereafter as MOR6654B or VAY736, or under its international non-proprietary name ianalumab.

SUMMARY OF THE DISCLOSURE

The benefits of B cell depletion therapy in autoimmune diseases have been well established, demonstrated primarily through experience with CD20-targeted depletion (Schioppo and Ingegnoli 2017). Evidence from clinical trials with the anti-CD20 mAb rituximab in autoimmune disease patients indicated that the more completely the B-cell are depleted, the better is the clinical response achieved, with the return of B cells post-depletion frequently coinciding with disease flares (Vital 2011).

A number of autoimmune diseases, including rheumatoid arthritis, Sjögren's, and SLE, are hypothesized to result from BAFF-driven B cell hyperactivity (Perosa 2010). Yet to varying degrees, these diseases resist treatment with anti-CD20 targeted B cell depleting agents such as rituximab, suggesting that more effective targeting of B cells is required.

Ianalumab is a human IgG1/κ mAb designed to target human BAFF-R and to competitively inhibit binding of BAFF to BAFF-R, thereby blocking BAFF-R-mediated signaling in B cells. In addition, ianalumab effectively eliminates B cells from circulation in vivo by antibody-dependent cytotoxicity (ADCC).

Therapeutic responses to B cell depletion therapy vary substantially between different diseases and for individuals within a given disease category, suggesting that more effective targeting of B cells is required. The use of ianalumab's dual mechanisms of action to deplete B cells by enhanced ADCC while concurrently suppressing B cell hyperactivity through BAFF:BAFF-R signaling blockade offers the possibility of achieving complementary or synergistic effects to raise clinical efficacy above that obtained by either of these mechanisms used as monotherapy.

We have now devised novel treatments for LN patients using an anti-BAFFR antibody, such as ianalaumab, that are safe, effective and provide sustained responses for patients. Importantly, because current SoC treatments for LN have strong immunosuppressive effects, any add-on therapy must maintain a favorable risk/benefit profile. Hence, these novel treatments satisfy a long-felt need of clinicians and patients for a safe, sustained, and effective therapy (particularly an add-on therapy) for LN. Ianalumab's dual mechanisms of action to directly deplete B cells and also suppress B cell hyperactivity offers the possibility of achieving effects to raise clinical efficacy above that obtained by either of these mechanisms alone.

The treatments for LN patients using an anti-BAFFR antibody, such as ianalaumab, as disclosed herein, are effective treatments achieving complete renal response (CRR) (defined as estimated glomerular filtration rate (eGFR) ≥90 mVmin/1.73 m2 or no less than 85% of baseline, AND, 24-hour UPCR <0.5).

The treatments for LN patients using an anti-BAFFR antibody, such as ianalaumab, as disclosed herein, are effective treatments achieving stable Overall Renal Response (ORR), defined as achievement as either Complete Renal Response (CRR) or Partial Renal Response (PRR).

The treatments for LN patients using an anti-BAFFR antibody, such as ianalaumab, as disclosed herein, are effective treatments achieving improvement in Functional Assessment of Chronic Illness Therapy (FACIT) Fatigue score (FACIT-Fatigue score).

The treatments for LN patients using an anti-BAFFR antibody, such as ianalaumab, as disclosed herein, are effective treatments showing reduction in moderate or severe disease flares (providing sustained versus partial BAFF-R blockade) over the dosing interval. This reduction is to assess flares by looking at the proportion of subjects remaining with absence of flare, reduction of event rate (annualized rate) and time to flare, with a focus on moderate and severe flares. A moderate or severe flare is defined as a clinically meaningful increase in disease activity using the BILAG score (1 new category A or 2 new category B items, respectively) that would most commonly involve some increase in therapy with cytotoxic agents and/or corticosteroids.

The treatments for LN patients using an anti-BAFFR antibody, such as ianalaumab, as disclosed herein, are effective treatments achieving Lupus Low Disease Activity State (LLDAS).

The treatments for LN patients using an anti-BAFFR antibody, such as ianalaumab, as disclosed herein, are effective treatments achieving occurrence of UPCR <(urine protein-to-creatinine ratio) (UPCR) 0.5 or ≥50% reduction from baseline.

In one embodiment, an anti-BAFFR antibody is provided, said antibody comprising an immunoglobulin VH domain comprising the amino acid sequence of SEQ ID NO: 1 and an immunoglobulin VL domain comprising the amino acid sequence of SEQ ID NO: 2, and wherein said antibody is to be administered to a subject in need thereof, as a dose of from about 50 mg to about 300 mg.

In a preferred embodiment, an anti-BAFFR designated VAY736 (ianalumab) is provided. Specifically, VAY736 (ianalumab) comprises the heavy chain amino acid sequence of SEQ ID NO: 9 and the light chain amino acid sequence of SEQ ID NO: 10, and wherein said antibody is to be administered to a subject in need thereof, as a dose of from about 50 mg to about 300 mg.

In one embodiment, the route of administration is subcutaneous or intravenous of the antibody according to the embodiments herein described, or a combination of subcutaneous or intravenous.

Some patients may benefit from a loading regimen (e.g., weekly for several weeks [e.g., 1 to 5 weeks, e.g., dosing at weeks 0, 1, 2, 3 and/or 4] or biweekly for several weeks (e.g., 2 to 8 weeks, e.g., dosing at weeks 0, 2, 4, and/or 6) followed by maintenance regimen, e.g. a monthly maintenance regimen. For example, an appropriate regimen for anti-BAFFR antibody can be weekly or bi-weekly for several weeks [e.g., 1 to 5 weeks, e.g., dosing at weeks 0, 1, 2, 3 and/or 4] followed by a monthly maintenance regimen.

In another example, an appropriate regimen for ianalumab is a monthly regimen.

In some embodiments, the anti-BAFFR antibody, such as ianalumab, may be administered to the patient at an initial dose of 300 mg delivered s.c., and the dose may be then adjusted if needed, as determined by a physician.

In one embodiment, the anti-BAFFR antibody, such as ianalumab, is administered at a dose of about 300 mg, s.c., every four (4) weeks (q4w).

In one embodiment, the anti-BAFFR antibody, such as ianalumab, is administered at a dose of about 300 mg, s.c., every twelve (12) weeks (q12w).

In yet another specific embodiment, a dose which comprises two unit doses of 150 mg ianalumab is administered s.c. every four (4) weeks (q4w).

Ianalumab may be administered quarterly, monthly, weekly or biweekly e.g. subcutaneously at a dosing of about 50 mg to 500 mg, e.g. about 150 mg to about 400 mg, e.g. about 150 mg to about 300 mg, or a e.g. about 200 mg to about 300 mg being administered, by subcutaneous injection, at an unit dose of about 50 mg, about 100 mg, about 150 mg, about 200 mg or about 300 mg. Ianalumab may be administered by subcutaneous injection, bi-weekly, or monthly at a dose of about 50 mg to about 300 mg, preferably about 300 mg.

As herein defined, 'unit dose' refers to a s.c. dose that can be comprised between about 50 mg to 500 mg, e.g. about 150 mg to about 400 mg, e.g. about 150 mg to about 300 mg, or a e.g. about 200 mg to about 300 mg. For example, an unit S.C. dose is about 50 mg, about 150 mg, about 150 mg, about 200 mg, about 250 mg, about 300 mg.

In one embodiment, the present invention comprises administering ianalumab to a patient with LN, in the range of about 50 mg to about 500 mg per treatment, preferably in the range of 50 mg to 300 mg, preferably in the range of 100 mg to 300 mg, preferably 150 mg to 300 mg per treatment. In one embodiment a patient receives 50 mg to 300 mg per treatment. In one embodiment patient receives 150 mg to 300 mg per treatment. In one embodiment patient receives 20 mg, 30 mg, 60 mg, 90 mg, 120 mg, 150 mg, 180 mg, 200 mg, 210 mg, 250 mg, 275 mg, or 300 mg per treatment. In one embodiment the patient with LN, receives each treatment every 2 weeks, every 3 weeks, monthly (every 4 weeks), every 6 weeks, bimonthly (every 2 months), every 9 weeks or quarterly (every 3 months). In one embodiment the patient receives each treatment every 3 weeks. In one embodiment the patient receives each treatment every 4 weeks.

When safety concern raises, the dose can be down-titrated, preferably by increasing the dosing interval, preferably by doubling or tripling the dosing interval. For example 300 mg monthly or every 3 weeks regimen can be doubled to every 2 month or every 6 weeks respectively or tripled to every 3 month or every 9 weeks respectively.

In some embodiments, the anti-BAFFR antibody or binding fragment thereof is to be administered in combination with one or more additional agents. In some embodiments, the one or more additional agents comprise standard-of-care (SoC) therapy for treatment of LN.

In another aspect, the disclosure provides new dosing regimens for anti-BAFFR antibodies (e.g., ianalumab) and binding fragments thereof that can be used in methods of treating LN.

In some embodiments, the anti-BAFFR antibody, such as ianalumab, may refer to antibodies which have demonstrated to be biosimilar to or interchangeable to ianalumab. Those antibodies may be administered according the embodiments which refer to ianalumab administration, as herein disclosed.

DETAILED DESCRIPTION OF THE DISCLOSURE

For purposes of interpreting this specification, the following definitions will apply and whenever appropriate, terms used in the singular will also include the plural and vice versa.

The term "comprising" encompasses "including" as well as "consisting," e.g., a composition "comprising" X may consist exclusively of X or may include something additional, e.g., X+Y.

Unless otherwise specifically stated or clear from context, as used herein, the term "about" in relation to a numerical value is understood as being within the normal tolerance in the art, e.g., within two standard deviations of the mean. Thus, "about" can be within +/−10%, 9%, 8%, 7%, 6%, 5%, 4%, 3%, 2%, 1%, 0.1%, 0.05%, or 0.01% of the stated value, preferably +/−10% of the stated value. When used in front of a numerical range or list of numbers, the term "about" applies to each number in the series, e.g., the phrase "about 1-5" should be interpreted as "about 1-about 5", or, e.g., the phrase "about 1, 2, 3, 4" should be interpreted as "about 1, about 2, about 3, about 4, etc."

The word "substantially" does not exclude "completely," e.g., a composition which is "substantially free" from Y may be completely free from Y. Where necessary, the word "substantially" may be omitted from the definition of the disclosure.

The term "antibody" as referred to herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three or four domains, depending on the isotype, CH1, CH2, CH3 and CH4. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen (e.g., a portion of BAFFR). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., 1989 Nature 341:544-546), which consists of a VH domain; and an isolated complementarity determining region (CDR).

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term “antigen-binding region” of an antibody. These antibody fragments are obtained using conventional techniques known to those of skill in the art, and the fragments are screened for utility in the same manner as are intact antibodies.

The term “BAFFR” refers to the B-cell activating factor receptor protein. BAFFR is also known as TNF Receptor Superfamily Member 13C (TNFRSFI3C). The human and murine amino acid and nucleic acid sequences can be found in a public database, such as GenBank, UniProt and Swiss-Prot. For example, an amino acid sequence of human BAFFR can be found as UniProt/Swiss-Prot Accession No. Q96RJ3 and a nucleotide sequences encoding human BAFFR can be found at Accession Nos. NM_052945.4. It is expressed predominantly on B-lymphocytes and on a subset of T-cells.

An “isolated antibody”, as used herein, refers to an antibody that is substantially free of other antibodies having different antigenic specificities, e.g., an isolated antibody that specifically binds human BAFFR is substantially free of antibodies that specifically bind antigens other than BAFFR. An isolated antibody that specifically binds BAFFR may, however, have cross-reactivity to other antigens, such as BAFFR molecules from other species. Moreover, an isolated antibody may be substantially free of other cellular material and/or chemicals.

The terms “monoclonal antibody” or “monoclonal antibody composition” as used herein refer to a preparation of antibody molecules of single molecular composition. A monoclonal antibody composition displays a single binding specificity and affinity for a particular epitope.

The term “human antibody”, as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik, et al. (2000. J Mol Biol 296, 57-86).

The precise amino acid sequence boundaries of a given CDR can be determined using any of a number of well-known schemes, including those described by Kabat et al. (1991), “Sequences of Proteins of Immunological Interest,” 5th Ed. Public Health Service, National Institutes of Health, Bethesda, MD (‘Kabat’ numbering scheme), Al-Lazikani et al., (1997) JMB 273, 927-948 (‘Chothia’ numbering scheme) and ImMunoGenTics (IMGT) numbering (Lefranc, M.-P., The Immunologist, 7, 132-136 (1999); Lefranc, M.-P. et al., Dev. Comp. Immunol., 27, 55-77 (2003) (‘IMGT’ numbering scheme). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to “Kabat”). Under IMGT, the CDR regions of an antibody can be determined using the program IMGT/DomainGap Align. Throughout this specification, the complementarity determining region (“CDR”) is defined according to the any of the above mentioned schemes.

The human antibodies of the invention may include amino acid residues not encoded by human sequences (e.g., mutations introduced by random or site-specific mutagenesis in vitro or by somatic mutation in vivo). However, the term “human antibody”, as used herein, is not intended to include antibodies in which CDR sequences derived from the germline of another mammalian species, such as a mouse, have been grafted onto human framework sequences.

The term “human monoclonal antibody” refers to antibodies displaying a single binding specificity which have variable regions in which both the framework and CDR regions are derived from human sequences.

The term “recombinant human antibody”, as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, “isotype” refers to the antibody class (e.g., IgM, IgA, IgD, IgE and IgG such as IgG1, IgG2, IgG3 or IgG4) that is provided by the heavy chain constant region genes.

The term “anti-BAFFR antibody or binding fragment thereof” as used herein refers to an antibody, or binding fragment thereof, which comprises a BAFFR binding domain. The binding of the antibody (or binding fragment thereof) to BAFFR inhibits the binding of BAFFR to BAFF and thereby reduces the formation of BAFF/BAFFR complexes, and/or reduce the activation of BAFFR. Suitably, the anti-BAFFR antibody or binding fragment thereof may reduce the formation of BAFF/BAFFR complexes and/or reduce the activation of BAFFR by at least 30%, at least 40%, at least 50%, at least 60%, at least 70%, at least 80%, at least 90%, at least 95%, at least 96%, at least 97%, at least 98%, at least 99%, or more as compared to a suitable control (for example a sample without the presence of an anti-BAFFR antibody or binding fragment thereof). Additionally or alternatively, an anti-BAFFR antibody or binding thereof may dissociate preformed BAFF/BAFFR complexes. In a suitable embodiment antibody or binding fragment thereof may dissociate at least 30%, at least 40%, at least 50%, at least 60%, at least 70%, at least 80%, at least 90%, at least 95%, at least 96%, at least 97%, at least 98%, at least 99%, or more of preformed BAFF/BAFFR complexes. As before, this property may be compared to a suitable control (for example a sample without the presence of an anti-BAFFR antibody or binding fragment thereof).

The phrase "pharmaceutically acceptable" as employed herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutical combination" as used herein means a product that results from the use or mixing or combining of more than one active ingredient. It should be understood that pharmaceutical combination as used herein includes both fixed and non-fixed combinations of the active ingredients.

The terms "co-administration" or "combined administration" or the like as utilized herein are meant to encompass the administration of one or more compounds described herein together with a selected combination partner to a single subject in need thereof (e.g., a patient or subject), and are intended to include treatment regimens in which the compounds are not necessarily administered by the same route of administration and/or at the same time.

The term "pharmaceutical composition" is defined herein to refer to a mixture (e.g., a solution or an emulsion) containing at least one active ingredient or therapeutic agent to be administered to a warm-blooded animal, e.g., a mammal or human, in order to prevent or treat a particular disease or condition affecting the warm-blooded animal.

The term "a therapeutically effective amount" of a compound of the present disclosure refers to an amount of the compound of the present disclosure that will elicit the biological or medical response of a subject (patient of subject), for example, reduction or inhibition of an enzyme or a protein activity, or ameliorate symptoms, alleviate conditions, slow or delay disease progression, or prevent a disease, etc. The therapeutically effective dosage of a compound, the pharmaceutical composition, or the combinations thereof, is dependent on the species of the patient, the body weight, age, sex, and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The phrase "therapeutic regimen" means the regimen used to treat an illness, e.g., the dosing protocol used during the treatment of LN. A therapeutic regimen may include an induction regimen and a maintenance regimen.

The term "dosing", as used herein, refers to the administration of a substance (e.g., an anti-BAFFR antibody) to achieve a therapeutic objective (e.g., the treatment of LN).

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

As used herein, the term "carrier" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

As used herein, the term 'subject' refers to an animal. Typically, the animal is a mammal.

A subject also refers to for example, primates (e.g., humans, male or female), cows, sheep, goats, horses, dogs, cats, rabbits, rats, mice, fish, birds and the like. In certain embodiments, the subject is a primate. In a preferred embodiment, the subject is a human. The term "subject" is used interchangeably with "patient" when it refers to human.

As used herein, a subject is "in need of" a treatment if such subject would benefit biologically, medically or in quality of life from such treatment.

As used herein, the phrase "population of patients" is used to mean a group of patients.

The term "comprising" encompasses "including" as well as "consisting," e.g., a composition "comprising" X may consist exclusively of X or may include something additional, e.g., X+Y.

AUCO-t designates the area under the plasma concentration-time curve from time zero to time 't' where t is a defined time point after administration [mass×time/volume].

AUCtx-ty represents the area under the plasma concentration-time curve from time 'x' to time 'y' where 'time x' and 'time y' are defined time points after administration.

Cmax is the observed maximum plasma concentration following drug administration [mass/volume].

Cmin is the observed minimum plasma concentration following drug administration

Ctrough is the observed plasma concentration that is just prior to the beginning of, or at the end of a dosing interval.

Tmax is the time to reach the maximum concentration after drug administration [time].

ss (subscript) indicate that the parameter is defined at steady state.

The phrase "means for administering" is used to indicate any available implement for systemically administering a drug to a patient, including, but not limited to, a pre-filled syringe, a vial and syringe, an injection pen, an autoinjector, an i.v. drip and bag, a pump, a patch pump, etc. With such items, a patient may self-administer the drug (i.e., administer the drug on their own behalf) or a physician may administer the drug.

The term "treatment" or "treat" is herein defined as the application or administration of a compound according to the disclosure, (an anti-BAFFR antibody, such as ianalumab), to a subject or to an isolated tissue or cell line from a subject, where the subject has a particular disease (e.g., LN), a symptom associated with the disease (e.g., LN), or a predisposition towards development of the disease (e.g., LN) (if applicable), where the purpose is to cure (if applicable), delay the onset of, reduce the severity of, alleviate, ameliorate one or more symptoms of the disease, improve the disease, reduce or improve any associated symptoms of the disease or the predisposition toward the development of the disease. The term "treatment" or "treat" includes treating a patient suspected to have the disease as well as patients who are ill or who have been diagnosed as suffering from the disease or medical condition, and includes suppression of clinical relapse.

As used herein, the phrase "population of patients" is used to mean a group of patients. In some embodiments of the disclosed methods, the anti-BAFFR antibody, such as ianalumab, is used to treat a population of LN patients.

As used herein, "selecting" and "selected" in reference to a patient is used to mean that a particular patient is specifically chosen from a larger group of patients on the basis of (due to) the particular patient having a predetermined criteria. Similarly, "selectively treating" refers to providing treatment to a patient having a particular disease, where that patient is specifically chosen from a larger group of patients on the basis of the particular patient having a predetermined criterion. Similarly, "selectively administering" refers to administering a drug to a patient that is specifically chosen from a larger group of patients on the basis of (due to) the particular patient having a predetermined criterion. By "selecting", "selectively treating" and "selectively administering", it is meant that a patient is delivered a personalized therapy based on the patient's personal history (e.g., prior therapeutic interventions, e.g., prior treatment with biologics), biology (e.g., particular genetic markers), and/or manifestation (e.g., not fulfilling particular diagnostic criteria), rather than being delivered a standard treatment regimen based solely on the patient's membership in a larger group. Selecting, in reference to a method of treatment as used herein, does not refer to fortuitous treatment of a patient having a particular criterion, but rather refers to the deliberate choice to administer treatment to a patient based on the patient having a particular criterion. Thus, selective treatment/administration differs from standard treatment/administration, which delivers a particular drug to all patients having a particular disease, regardless of their personal history, manifestations of disease, and/or biology. In some embodiments, the patient was selected for treatment based on having LN.

In some embodiments, the patient is selected for treatment based on having LN, e.g., ISN/RPS Class III or IV LN. In some embodiments, the patient is selected for treatment based on having active LN. In some embodiments, the patient is selected for treatment based on having previously had an inadequate response to a standard-of-care LN therapy.

Anti-BAFFR Antibodies

Antibodies against BAFFR ("anti-BAFFR antibodies") are known from e.g. WO 2010/007082 and include antibodies which are characterized by comprising a VH domain with the amino acid sequence of SEQ ID NO: 1 and a VL domain with the amino acid sequence of SEQ ID NO: 2. The antibody MOR6654 is one such antibody (IgG1 kappa). It has the heavy chain amino acid sequence of SEQ ID NO: 9 and the light chain amino acid sequence of SEQ ID NO: 10. This antibody may be expressed from SEQ ID NOs: 13 and 14, preferably in a host cell which lacks fucosyl-transferase, for example in a mammalian cell line with an inactive FUT8 gene (e.g. FUT8−/−), to provide a functional non-fucosylated anti-BAFFR antibody with enhanced ADCC. This antibody is referred to hereafter as MOR6654B or VAY736, or under its international non-proprietary name ianalumab. Alternative ways to produce non-fucosylated antibodies are known in the art. Amino acid sequences for ianalumab are shown in Table 1, together with nucleic acid sequences encoding ianalumab heavy and light chains.

TABLE 1 ianalumab sequences

| Portion | Amino acid or Nucleotide Sequence |
|---|---|
| VH | QVQLQQSGPGLVKPSQTLSLTCAISGDSVSSNSAAWGWIRQSPGRGLEW LGRIYYRSKWYNSYAVSVKSRITINPDTSKNQFSLQLNSVTPEDTAVYY CARYDWVPKIGVFDSWGQGTLVTVSS (SEQ ID NO: 1) |
| VL | DIVLTQSPATLSLSPGERATLSCRASQFISSSYLSWYQQKPGQAPRLLI YGSSSRATGVPARFSGSGSGTDFTLTISSLEPEDFAVYYCQQLYSSPMT FGQGTKVEIK (SEQ ID NO: 2) |
| CDR-H1 | GDSVSSNSAAWG (SEQ ID NO: 3) |
| CDR-H2 | RIYYRSKWYNSYAVSVKS (SEQ ID NO: 4) |
| CDR-H3 | YDWVPKIGVFDS (SEQ ID NO: 5) |
| CDR-L1 | RASQFISSSYLS (SEQ ID NO: 6) |
| CDR-L2 | GSSSRAT (SEQ ID NO: 7) |
| CDR-L3 | QQLYSSPMT (SEQ ID NO: 8) |

TABLE 1-continued

| ianalumab sequences | |
|---|---|
| Portion | Amino acid or Nucleotide Sequence |
| Heavy Chain | QVQLQQSGPGLVKPSQTLSLTCAISGDSVSSNSAAWGWIRQSPGRGLEW<br>LGRIYYRSKWYNSYAVSVKSRITINPDTSKNQFSLQLNSVTPEDTAVYY<br>CARYDWVPKIGVFDSWGQGTLVTVSSASTKGPSVFPLAPSSKSTSGGTA<br>ALGCLVKDYFPEPVTVSWNSGALTSGVHTFPAVLQSSGLYSLSSVVTVP<br>SSSLGTQTYICNVNHKPSNTKVDKRVEPKSCDKTHTCPPCPAPELLGGP<br>SVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTI<br>SKAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALHN<br>HYTQKSLSLSPGK (SEQ ID NO: 9) |
| Light Chain | DIVLTQSPATLSLSPGERATLSCRASQFISSSYLSWYQQKPGQAPRLLI<br>YGSSSRATGVPARFSGSGSGTDFTLTISSLEPEDFAVYYCQQLYSSPMT<br>FGQGTKVEIKRTVAAPSVFIFPPSDEQLKSGTASVVCLLNNFYPREAKV<br>QWKVDNALQSGNSQESVTEQDSKDSTYSLSSTLTLSKADYEKHKVYACE<br>VTHQGLSSPVTKSFNRGEC (SEQ ID NO: 10) |
| Nucleotide sequence encoding SEQ ID NO: 1 | CAGGTGCAGCTGCAGCAGAGCGGCCCAGGCCTGGTCAAGCCCTCTCAGA<br>CCCTGTCACTGACCTGCGCCATTTCAGGCGACAGCGTGAGCAGCAACAG<br>CGCCGCCTGGGGCTGGATCAGGCAGAGCCCCGGTAGGGGCCTGGAATGG<br>CTGGGCAGGATCTACTACAGGTCCAAGTGGTACAACAGCTACGCCGTGA<br>GCGTGAAGAGCAGGATCACCATCAACCCTGACACCAGCAAGAACCAGTT<br>CTCACTGCAGCTCAACAGCGTGACCCCCGAGGACACCGCCGTGTACTAC<br>TGCGCCAGATACGACTGGGTGCCCAAGATCGGCGTGTTCGACAGCTGGG<br>GCCAGGGCACCCTGGTGACCGTGTCAAGC (SEQ ID NO: 11) |
| Nucleotide sequence encoding SEQ ID NO: 1 | GATATCGTGCTGACACAGAGCCCCGCCACCCTGAGCCTGAGCCCAGGCG<br>AGAGGGCCACCCTGTCCTGCAGGGCCAGCCAGTTTATCAGCAGCAGCTA<br>CCTGTCCTGGTATCAGCAGAAGCCCGGCCAGGCCCCTAGACTGCTGATC<br>TACGGCAGCTCCTCTCGGGCCACCGGCGTGCCCGCCAGGTTCAGCGGCA<br>GCGGCTCCGGCACCGACTTCACCCTGACAATCAGCAGCCTGGAGCCCGA<br>GGACTTCGCCGTGTACTACTGCCAGCAGCTGTACAGCTCACCCATGACC<br>TTCGGCCAGGGCACCAAGGTGGAGATCAAG (SEQ ID NO: 12) |
| Full length nucleotide sequence (including leader sequence and constant part) of heavy chain; nt 1-57 = leader; nt 58-429 = VH; nt 430-1419 = constant region (hIgG1) | ATGGCCTGGGTGTGGACCCTGCCCTTCCTGATGGCCGCTGCCCAGTCAG<br>TGCAGGCCCAGGTGCAGCTGCAGCAGAGCGGCCCAGGCCTGGTCAAGCC<br>CTCTCAGACCCTGTCACTGACCTGCGCCATTTCAGGCGACAGCGTGAGC<br>AGCAACAGCGCCGCCTGGGGCTGGATCAGGCAGAGCCCCGGTAGGGGCC<br>TGGAATGGCTGGGCAGGATCTACTACAGGTCCAAGTGGTACAACAGCTA<br>CGCCGTGAGCGTGAAGAGCAGGATCACCATCAACCCTGACACCAGCAAG<br>AACCAGTTCTCACTGCAGCTCAACAGCGTGACCCCCGAGGACACCGCCG<br>TGTACTACTGCGCCAGATACGACTGGGTGCCCAAGATCGGCGTGTTCGA<br>CAGCTGGGGCCAGGGCACCCTGGTGACCGTGTCAAGCGCCAGCACCAAG<br>GGCCCCAGCGTGTTCCCCCTGGCCCCCAGCAGCAAGAGCACCAGCGGCG<br>GCACAGCCGCCCTGGGCTGCCTGGTGAAGGACTACTTCCCCGAGCCCGT<br>GACCGTGTCCTGGAACAGCGGAGCCCTGACCTCCGGCGTGCACACCTTC<br>CCCGCCGTGCTGCAGAGCAGCGGCCTGTACAGCCTGTCCAGCGTGGTGA<br>CAGTGCCCAGCAGCAGCCTGGGCACCCAGACCTACATCTGCAACGTGAA<br>CCACAAGCCCAGCAACACCAAGGTGGACAAGAGAGTGGAGCCCAAGAGC<br>TGCGACAAGACCCACACCTGCCCCCCCTGCCCAGCCCCAGAGCTGCTGG<br>GCGGACCCTCCGTGTTCCTGTTCCCCCCCAAGCCCAAGGACACCCTGAT<br>GATCAGCAGGACCCCCGAGGTGACCTGCGTGGTGGTGGACGTGAGCCAC<br>GAGGACCCAGAGGTGAAGTTCAACTGGTACGTGGACGGCGTGGAGGTGC<br>ACAACGCCAAGACCAAGCCCAGAGAGGAGCAGTACAACAGCACCTACAG<br>GGTGGTGTCCGTGCTGACCGTGCTGCACCAGGACTGGCTGAACGGCAAG<br>GAATACAAGTGCAAGGTCTCCAACAAGGCCCTGCCAGCCCCCATCGAAA<br>AGACCATCAGCAAGGCCAAGGGCCAGCCACGGGAGCCCCAGGTGTACAC<br>CCTGCCCCCCTCCCGGGAGGAGATGACCAAGAACCAGGTGTCCCTGACC<br>TGTCTGGTGAAGGGCTTCTACCCCAGCGACATCGCCGTGGAGTGGGAGA<br>GCAACGGCCAGCCCGAGAACAACTACAAGACCACCCCCCCAGTGCTGGA<br>CAGCGACGGCAGCTTCTTCCTGTACAGCAAGCTGACCGTGGACAAGTCC<br>AGGTGGCAGCAGGGCAACGTGTTCAGCTGCAGCGTGATGCACGAGGCCC<br>TGCACAACCACTACACCCAGAAGAGCCTGAGCCTGTCCCCCGGCAAG<br>(SEQ ID NO: 14) |

TABLE 1-continued

| ianalumab sequences | |
|---|---|
| Portion | Amino acid or Nucleotide Sequence |
| Full length nucleotide sequence (including leader sequence and constant part) of light chain; nt 1-60 = leader; nt 61-384 = VL; nt 385-705 = constant region (hkappa) | ATGAGCGTGCTGACCCAGGTGCTGGCTCTGCTGCTGCTGTGGCTGACCG GCACCAGATGCGATATCGTGCTGACACAGAGCCCCGCCACCCTGAGCCT GAGCCCAGGCGAGAGGGCCACCCTGTCCTGCAGGGCCAGCCAGTTTATC AGCAGCAGCTACCTGTCCTGGTATCAGCAGAAGCCCGGCCAGGCCCCTA GACTGCTGATCTACGGCAGCTCCTCTCGGGCCACCGGCGTGCCCGCCAG GTTCAGCGGCAGCGGCTCCGGCACCGACTTCACCCTGACAATCAGCAGC CTGGAGCCCGAGGACTTCGCCGTGTACTACTGCCAGCAGCTGTACAGCT CACCCATGACCTTCGGCCAGGGCACCAAGGTGGAGATCAAGCGTACGGT GGCCGCTCCCAGCGTGTTCATCTTCCCCCCCAGCGACGAGCAGCTGAAG AGCGGCACCGCCAGCGTGGTGTGCCTGCTGAACAACTTCTACCCCCGGG AGGCCAAGGTGCAGTGGAAGGTGGACAACGCCCTGCAGAGCGGCAACAG CCAGGAGAGCGTCACCGAGCAGGACAGCAAGGACTCCACCTACAGCCTG AGCAGCACCCTGACCCTGAGCAAGGCCGACTACGAGAAGCATAAGGTGT ACGCCTGCGAGGTGACCCACCAGGGCCTGTCCAGCCCCGTGACCAAGAG CTTCAACAGGGGCGAGTGC (SEQ ID NO: 15) |

In some embodiments, the anti-BAFFR antibody or binding fragment thereof comprises a heavy chain variable region comprising three CDRs having sequences of SEQ ID NO: 3, SEQ ID NO: 4, and SEQ ID NO: 5, respectively, and a light chain variable region comprising three CDRs having sequences of SEQ ID NO: 6, SEQ ID NO: 7, and SEQ ID NO: 8, respectively. In a preferred embodiment, the anti-BAFFR antibody or binding fragment thereof comprises a heavy chain variable region consisting of the sequence SEQ ID NO: 1 and a light chain variable region consisting of the sequence SEQ ID NO: 2. In a more preferred embodiment, the anti-BAFFR antibody or binding fragment thereof is ianalumab or binding fragment thereof.

Methods of Treatment and Uses of Anti-BAFFR Antibodies or Antigen-Binding Fragments Thereof, e.g. Ianalumab The disclosed the anti-BAFFR antibody or antigen-binding fragment, (e.g. ianalumab), may be used in vitro, ex vivo, or incorporated into pharmaceutical compositions and administered in vivo to treat LN patients (e.g., human patients).

LN is categorized histologically into six classes by the International Society of Nephrology/Renal Pathology Society (ISN/RPS) classification system that has become the standard for renal biopsy interpretation because of improved correlation with prognostic and therapeutic outcomes (Weening et al., 2004; J Am Soc Nephrol; 15(2):241-50; Markowitz et al., 2007 Kidney Int; 71(6):491). Treatments include management with corticosteroids for lower stage disease, followed by more aggressive immunosuppressive therapies for more severe disease and ultimately renal transplant.

Class I and II LN is present in approximately 10.2 to 25.7% of patients with LN and is characterized by immune-complexes that form within the mesangium by binding of antibodies to autoantigens (Wang et al., 2018 Arch Rheumatol; 33(1):17-25). Patients with class I minimal mesangial LN display normal glomeruli by light microscopy, but mesangial immune deposits are visible by immunofluorescence. Patients with LN class I and II usually have a more favorable prognosis than with other classes of LN. Class I and II LN are usually managed with corticosteroids (Yu et al., 2017 Nat Rev Nephrol; 13(8):483-495).

Class III and IV LN is detected in approximately 39 to 71.9% of LN patients and is the result of the deposition of immune complexes in the subendothelial space of the glomerular capillaries (Wang et al., 2018 Arch Rheumatol; 33(1):17-25). Both classes are considered to have similar lesions that differ by severity and distribution. Class IV diffuse LN is distinguished from class III on the basis of involvement of more than 50% of glomeruli with endocapillary lesions. Patients with class III and IV LN require aggressive therapy with glucocorticoids and immunosuppressive agents (Hahn et al. (2012) Arthritis Care Res 64:797-808).

Class V LN, also known as membranous lupus nephritis, is present in approximately 12.1 to 20.3% of patients with LN and is characterized by the deposition of immune complexes in the subepithelial compartment of the glomeruli (Wang et al., 2018 Arch Rheumatol; 33(1):17-25). Class V LN, when combined with III or IV, should be treated in the same manner as III or IV.

Class VI LN represents 1.3 to 4.7% of LN patients and is characterized by the development of sclerotic lesions and leads to irreversible glomerulosclerosis (Wang et al., 2018 Arch Rheumatol; 33(1):17-25). With class VI LN, the progression of renal fibrosis and sclerosis is usually associated with a progressive decline in glomerular filtration rate and ultimately the development of ESRD. Histologic class VI (sclerosis of 290% of glomeruli) generally requires preparation for renal replacement therapy rather than immunosuppression.

Class III and IV LN have subgroups of “A” (active lesions), “C” (chronic lesions) and A/C (active and chronic lesions). (Hahn et al. (2012)). As per the revision of the pathological classification of LN, categorizing class IV into segmental or global subdivisions (“IV-S” and “IV-G”) are to be eliminated due to limitation of reproducibility of the information and weak clinical significance. The newly proposed modifications of the NIH LN activity and chronicity scoring system also recommends a semi-quantitative approach to describe active and chronic lesions instead of “A”, “C”, and “A/C” parameters and new definitions for mesangial hypercellularity and for cellular, fibrocellular, and fibrous crescents (Bajema et al (2018). Kidney International; 93(4):789-796).

In some embodiments, the LN patient to be treated using the disclosed methods, uses, kits, etc. has International Society of Nephrology/Renal Pathology Society (ISN/RPS) Class III or IV LN. In some embodiments, the LN patient to be treated using the disclosed methods, uses, kits, etc. has ISN/RPS Class III or IV LN with or without co-existing features of Class V LN. In some embodiments, the LN patient to be treated using the disclosed methods, uses, kits, etc. has ISN/RPS Class III or IV LN, but not Class III(C), Class IV-S(C) or IV-G(C) LN. In other embodiments, the LN patient to be treated using the disclosed methods, uses, kits, etc. has ISN/RPS Class III or IV LN, but not chronic Class III or Class IV LN. As used herein, the phrase "features of Class V LN" refers to the disease aspects (e.g., histological, pathological, etc.) of Class V LN as provided by the ISN/RPS (see, e.g., Weening et a. (2004) Kidney Int. 65:521-530 and Weening et a. (2004) J Am Soc Nephrol. 15:241-250).

In some embodiments of the disclosed methods, kits, and uses, the LN patient to be treated has a renal biopsy showing active glomerulonephritis WHO or ISN/RPS Class III or IV LN [excluding III (C), IV-S(C) and IV-G (C)], with or without co-existing class V features, and whose disease has been inadequately controlled with previous SoC treatment (s).

As used herein, the phrase "active LN" refers to LN of the following criteria: biopsy results indicating active glomerulonephritis WHO or ISN/RPS Class III or IV LN [excluding III (C), IV-S (C) and IV-G (C)], with or without co-existing Class V; UPCR 21 prior to treatment; estimated eGFR >30 mL/min/1.73 m2 by Chronic Kidney Disease Epidemiology Collaboration (CKD-EPI) (see Levy et al. (2009) Ann Intern Med 150(9):604-612; Martinez-Martinez (2012) Rheumatol Int 32: 2293); and active urinary sediment (presence of cellular casts (granular or red blood cell casts) or hematuria (>5 red blood cells per high power field)). In some embodiments of the disclosed methods, kits, and uses, the LN patient to be treated has active LN.

As used herein, the phrases "inadequately controlled", "inadequate response", and the like refer to treatments that produce an insufficient response in a patient, e.g., the LN patient still has one or more pathological symptoms of LN, e.g., renal dysfunction, nephrotic syndrome, elevated urinary cast, urine protein, elevated urinary sediment, hematuria, nephropathy, etc. In some embodiments, prior to administering the anti-BAFFR antibody, the patient has had an inadequate response to prior treatment with a standard-of-care LN therapy. In some embodiments of the disclosure, an inadequate response is indicated by the LN patient having a UPCR >1 and active urinary sediment (presence of cellular [granular or red blood cell] cast) or hematuria (>5 red blood cells per high power field). In some embodiments, the LN patient to be treated using the disclosed methods, uses, kits, etc. has LN that has been inadequately controlled with previous SoC treatment(s).

A patient who has responded adequately to treatment with a standard-of-care LN therapy but has discontinued due to a side effect is termed "intolerant". In some embodiments, the LN patient to be treated using the disclosed methods, uses, kits, etc. is intolerant to a standard-of-care LN therapy.

As used herein, "standard-of-care (SoC) LN therapy" refers to a treatment regimen employing LN agents typically employed by health care professionals, including immunosuppressants and steroids (e.g., corticosteroids, e.g., glucocorticoids, e.g., prednisolone, prednisone, methylprednisolone, etc.), e.g., mycophenolate mofetil (MMF), cyclosporine A, rituximab, ocrelizumab, abatacept, azathioprine, calcineurin inhibitors, cyclosporine A, tacrolimus, cyclophosphamide (CYC), mycophenolic acid (MPA) (including salts thereof), voclosporin, belimumab, ustekinumab, iguratimod, anifrolumab, B1655064, and combination thereof. Steroids for treating LN may be given by IV pulse or orally, and are preferably corticosteroids, e.g., glucocorticoids, e.g., prednisolone, prednisone, methylprednisolone, etc. Doses and regimens of these LN agents (both induction and maintenance doses and regimens) are known to clinicians and may be found in, e.g., Hahn et al. (2012) Arthritis Care Res (Hoboken) 64(6): 797-808. In some embodiments, LN steroid therapy comprises pulse intravenous corticosteroid therapy where indicated, e.g., 500-1000 mg methylprednisolone daily for three doses, followed by daily oral glucocorticoids (0.5-1 mg/kg/day). In some embodiments, LN immunosuppressant therapy comprises an MMF dose of up to 3 g daily. In some embodiments, LN immunosuppressant therapy comprises a CYC dose of up to 15 mg/kg daily. As used herein, "mycophenolic acid (MPA)" refers to mycophenolate mofetil (MMF) or enteric-coated MPA sodium at equivalent dose. In some embodiments, during treatment with the anti-BAFFR antibody or a binding fragment thereof, the dose of MPA administered to the patient is reduced, and the patient does not experience a flare as a result of said reduction.

The most preferred standard-of-care LN therapy employs MPA (MMF or enteric coated MPA sodium) or CYC, along with corticosteroids for class III/IV LN patients for induction (Hahn et al (2012) Arthritis Care Res 64:797-808; Bertsias et al (2012) Ann Rheum Dis; 71, 1771-1782) as well as maintenance therapy after inducing remission (Palmer et al (2017) Am J Kidney Dis; 70(3):324-336). For example:

- low-dose CYC induction treatment typically consists of 6 administrations of 500 mg intravenous (i.v.) CYC every 2 weeks;
- MMF induction dose is typically up to 3 g daily (preferably 2 g daily) or equivalent dosage of enteric coated MPA sodium up to 2,160 mg daily (preferably 1440 mg daily) (Zeher et al (2011) Lupus 20(14):1484-93; Jones et al (2014) Clin Kidney J (2014) 7: 562-568) is favored for those patients with class III/IV and crescents, and for those patients with proteinuria and a recent significant rise in creatinine.

Pulse i.v. corticosteroid is typically 500-1000 mg methylprednisolone daily for 3 doses, followed by daily oral glucocorticoids (0.3-1 mg/kg/day, preferably 0.3 mg/kg/day-0.5 mg/kg/day) followed by a taper to the minimal amount necessary to control disease.

As used herein, "induction" refers to the portion of a LN therapy that induces remission of the disease. Preferred induction treatments include administration of MPA or CYC to the patient. Induction for MPA is typically 6 months and for CYC is typically 12 weeks. Thereafter, a patient is treated with a 'maintenance' regimen to maintain the patient in a disease-free (or relapse-free) state. A typical standard-of-care LN therapy may employ, e.g., induction: MMF 2-3 g per day for 6 months or CYC+glucocorticoid IV pulse for 3 days, then prednisone orally at 0.5-1 mg/kg per day tapered after a few weeks to the lowest effective dose; maintenance (if improvement after induction): MMF 1-2 g per day or AZA 2 mg/kg/day+−low-dose daily glucocorticoid. In some embodiments, the target dose during the maintenance period is 1-2 g/day of MMF or of equivalent dosage of enteric-coated MPA. Further reduction of MMF to 0.5 g/day or of equivalent dosage of enteric-coated MPA is also within the scope of the disclosure. In some embodiments, patients will also receive a maintenance dose of oral corticosteroids, with a target dose of 5 mg/day (2.5-7.5 mg/day acceptable dose range) from Week 16.

In one embodiments of the disclosure, the anti-BAFFR antibody or antigen-binding fragment, (e.g., ianalumab) is employed during maintenance therapy as an 'add-on' to standard-of-care in adult patients with active LN. In other embodiments of the disclosure, the anti-BAFFR antibody or antigen-binding fragment, (e.g., ianalumab) is employed during both induction and maintenance therapy as an "add-on" to standard-of-care in adult patients with active LN.

As used herein the term "flare," in the context of a LN flare (also referred to as a "renal flare") is as described in Parikh et al. (2014) Clin. J. Am. Soc. Nephrol. 9(2):279-84, i.e., an increase in LN disease activity requiring alternative or more intensive treatment. In some embodiments of the disclosure, treatment according to the disclosed methods, kits, uses, etc. with the anti-BAFFR antibody or antigen-binding fragment, (e.g., ianalumab) prevents LN flares, decreases the severity of LN flares, and/or decreases the frequency of LN flares.

The effectiveness of an LN treatment may be assessed using various known methods and tools that measure kidney disease state and/or kidney activity. Such tests include, e.g., glomerular filtration rate (GFR) or estimated GFR (eGFR), serum creatinine measurements, measurement of cellular casts, determination of urinary protein:urinary creatinine ratio (UPCR).

A urinary protein:urinary creatinine ratio (UPCR) (preferably done as part of a 24-hour urine test) refers to a diagnostic test that examines the ratio of the level of protein to creatinine in a sample from a patient's urine.

An estimated glomerular filtration rate (eGFR) may be measured by the Chronic Kidney Disease Epidemiology Collaboration (CKD-EPI) equation (Martinez-Martinez et al. (2012) Nefrologia 33(1):99-106); Levey et al. (2009) Ann Intern Med. 150(9) 604-12))

In some embodiments, the LN patient achieves a complete renal response (CRR) or a partial renal response (PRR).

As used herein, the phrase "complete renal response (CRR)" refers to a preferred outcome for therapy in LN, e.g., using the disclosed anti-BAFFR antibodies (e.g. ianalumab). It is demonstrated by clinically significant improvement of renal function. In preferred embodiments, CRR is achieved when the following two conditions are met: 1) estimated glomerular filtration rate (eGFR) is within the normal range or no less than 85% of baseline; and 2) 24-hour urinary protein to creatinine ratio (UPCR) s 0.5 mg/mg.

By "adequate response to a steroid daily dose" is meant that the patient does not experience a relapse or LN flare while treated with a particular daily dose of steroid. The dose that achieves this adequate response is referred to as a "stable dose". As used herein, the phrase "achieve a daily steroid dose of X following a steroid tapering regimen" means that a patient can utilize a stable steroid dose X after an original dose is tapered to X.

As used herein "steroid tapering", "taper", "tapering regimen" and the like refer to a reduction regimen of a steroid (e.g., corticosteroid, e.g., glucocorticoid, e.g., prednisone, prednisolone, methylprednisolone) given to a patient over time. The tapering schedule (timing and dose decrease) will depend on the original steroid (e.g., corticosteroid, e.g., glucocorticoid, e.g., prednisone, prednisolone, methylprednisolone) dose the patient is taking prior to treatment with the anti-BAFFR antibody or antigen-binding fragment, (e.g., ianalumab). A tapering regimen is in alignment with common medical practice in LN and is designed to minimize steroid related toxicity. Steroid tapering is a key goal to achieve in patients with LN given that the current SoC LN treatment regimens have substantial side effects from glucocorticoids and prolonged immunosuppression (Schwartz (2014). Curr Opin Rheumatol; 26: 502-509). In some embodiments of the disclosure, during treatment with the anti-BAFFR antibody or antigen-binding fragment, (e.g., ianalumab), the dose of steroid (e.g., corticosteroid, e.g., glucocorticoid, e.g., prednisone, prednisolone, methylprednisolone) administered to the patient is reduced using a taper regimen, and the patient does not experience a flare as a result of said reduction. In some embodiments of the disclosure, when said method is used to treat a population of patients with LN, at least 50% of said patients achieve a daily steroid dose of <10 mg/day following a steroid tapering regimen during treatment with the anti-BAFFR antibody or antigen-binding fragment, (e.g., ianalumab). In some embodiments of the disclosure, when said method is used to treat a population of patients with LN, at least 50% of said patients achieve a daily steroid dose of <5 mg/day following a steroid tapering regimen during treatment with the anti-BAFFR antibody or antigen-binding fragment, (e.g., ianalumab).

As used herein, the phrase "partial renal response (PRR)" refers to a preferred outcome for therapy in LN. PRR, adapted from Bertsias et al (2012) Ann Rheum Dis; 71, 1771-1782, is defined as: 1. ≥50% reduction in proteinuria to sub-nephrotic levels; and 2. normal or near-normal eGFR (285% of baseline) is achieved no later than 12 months following treatment initiation. PRR, adapted from Wofsy et al. (2013) Arthritis Rheum; 65(6): 1586-1591, is defined as: 1. for patients with UPCR >3 at baseline, reduction in UPCR to <3; or for patients with UPCR ≤3 at baseline, reduction in UPCR of at least 50% or final UPCR <1; and 2. reduced serum creatinine relative to baseline or an increase in serum creatinine of not more than 15% above baseline. In preferred embodiments, the treated patient achieves a PRR defined as: 1) an eGFR within the normal range or no less than 85% of baseline, and 2) 250% reduction in 24-hour UPCR to sub-nephrotic level compared to baseline Success of treatment overtime may be measured by various techniques and surveys, including assessment of CRR, PRR, steroid reduction, eGFR, Urine Albumin-to-Creatinine Ratio (UACR), UPCR, FACIT-Fatigue score (Cella et al (1993) J. Clin. Oncol; 11(3):570-9, Yellen et al (1997) J Pain Symptom Manage; 13(2):63-74), Short Form Health Survey (SF-36) (Holloway et al (2014) Health Qual Life Outcomes; 12:116), Medical Outcome Short Form Health Survey (SF-36 Physical Component Summary (PCS)) (Ware et al (1994) SF-36 Health Survey manual and interpretation guide. Update. Boston: The Health Institute, New England Medical Center), LupusQoL (Yazdany (2011) Arthritis Care Res 63(11):S413-9), improvement in multiple lupus domains, e.g., SLEDAI-2000 (Bombardier et al (1992) 35(6):630-40), CLASI (Albrecht et al (2005) J. Invest. Dermatol; 125:889-94), DAS-28 (Ceccarelli et al (2014) Scientific World Journal; article ID: 236842; Cipriano (2015) Reumatismo; 62(2):62-7), LLDAS (Franklyn et al (2016) Ann. Rheum. Dis; 75(9):1615-21).

A chronic, moderate-to-severe active SLE is defined as having:

SLEDAI-2K ≥6 (Touma 2010, Gladman 2002), excluding points attributed to "fever", "lupus headache" and "organic brain syndrome";

BILAG-2004 score of at least one "A" in either the mucocutaneous domain or in the musculoskeletal domain, or one "B" in either the mucocutaneous domain and at least one "A" or "B" in a second domain.

The SRI-4 is a composite endpoint, which has become a 'standard' outcome used by clinicians and Health Authorities to evaluate efficacy of treatments of SLE. It combines scores for a reduction in disease activity, a non-worsening of overall condition and non-recruitment of a new organ system, expressed as a responder rate. An SRI-4 response is defined by achieving all of the following:

A ≥4-point reduction from baseline in SLEDAI-2K (i.e., less disease activity) AND No new BILAG-2004 A score and ≤1 new BILAG-2004 B domain score (i.e., no new flares) AND No decline in Physician's Global Assessment, defined as an increase of ≥0.3 from baseline on a 0 to 3 visual analog scale (i.e., no worsening of disease).

The SRI-6 provides a more stringent requirement: instead of using a SLEDAI-2K criterion of 4 as the minimum threshold of disease activity required in the responder analyses, this SLEDAI-2K component of the SRI score is raised to ≥6.

The Lupus Low Disease Activity State (LLDAS) consists of five items that include disease activity and maintenance medication:

1. SLEDAI-2K ≤4, with no major organ system activity;
2. no new features of lupus disease activity compared to the prior assessment;
3. SELENA-SLEDAI PGA ≤1;
4. current predniso(lo)ne (or equivalent) dose ≤7.5 mg daily; and
5. well-tolerated standard maintenance doses of appropriate, non-investigational drugs.

As used herein, the term "baseline" and the like (e.g., "baseline value") refer to the value of a given variable prior to a subject being treated, e.g., with a disclosed anti-BAFFR antibody, e.g. ianalumab.

As used herein, the phrase "inactive urinary sediment" is a measure referring to a urine test, typically undertaken by centrifuging urine to concentrate substances, wherein there are <5 red blood cells and/or white blood cells per high power field (hpf). See, e.g., Cavanaugh and Perazella (2019) Am J. Kid. Diseases. 73(2):258-72.

As used herein, the phrase "cellular cast" refers to small tube-shaped particles made of cells (e.g., white blood cells, red blood cells, kidney cells) that can be found when urine is examined under the microscope during urinalysis. See, e.g., Ringsrud (2001) "Casts in the Urine Sediment" Laboratory Medicine (4)32.

In some embodiments, the patient is an adult human patient having LN. Is some embodiments, the patient is a pediatric human patient having LN. The upper age limit used to define a pediatric patient varies among experts, and can include adolescents up to the age of 21 (see, e.g., Berhman et a. (1996) Nelson Textbook of Pediatrics, 15th Ed. Philadelphia: W.B. Saunders Company; Rudolph A M, et al. (2002) Rudolph's Pediatrics, 21st Ed. New York: McGraw-Hill; and Avery (1994) First LR. Pediatric Medicine, 2nd Ed. Baltimore: Williams & Wilkins). As used herein, the term 'Pediatric' generally refers to a human who is sixteen years old or younger, which is the definition of a pediatric human used by the US FDA.

In some embodiments, the patient is an human patient having active LN (ISN/RPS class III, IV active glomerulonephritis with or without co-existing class V features, or pure class V membranous).

In some embodiments, the pediatric patient is administered a SC dose of the anti-BAFFR antibody, e.g. ianalumab, every four weeks (monthly) as a dose of about 150 mg-about 300 mg (e.g., 150 mg or 300 mg), regardless of the patient's weight.

In some embodiments, the pediatric patient is administered a SC dose of the anti-BAFFR antibody, e.g. ianalumab, every four weeks, as a dose of about 75 mg if the patient weighs <25 kg or about 150 mg if the patient weighs >25 kg.

In some embodiments, the pediatric patient is administered a SC dose of the anti-BAFFR antibody, e.g. ianalumab, every four weeks as a dose of about 150 mg or about 300 mg.

In some embodiments, the pediatric patient is administered a SC dose of the anti-BAFFR antibody, e.g. ianalumab, every four weeks as a dose of about 300 mg.

In some embodiments, the pediatric patient is administered an IV dose of anti-BAFFR antibody, e.g. ianalumab, of about 3 mg/kg-about 9 mg/kg.

Pharmaceutical Composition

Pharmaceutical compositions for use in the disclosed methods may be manufactured in conventional manner.

The anti-BAFFR antibody or antigen-binding fragment, (e.g., ianalumab), may be used as a pharmaceutical composition when combined with a pharmaceutically acceptable carrier. Such a composition may contain, in addition to the anti-BAFFR antibody, carriers, various diluents, fillers, salts, buffers, stabilizers, solubilizers, and other materials known in the art. The characteristics of the carrier will depend on the route of administration. The pharmaceutical compositions for use in the disclosed methods may also contain additional therapeutic agents for treatment of the particular targeted disorder. For example, a pharmaceutical composition may also include anti-inflammatory agents. Such additional factors and/or agents may be included in the pharmaceutical composition to produce a synergistic effect with the anti-BAFFR antibody, e.g., ianalumab. In preferred embodiments, the pharmaceutical compositions for use in the disclosed methods comprise ianalumab at 150 mg/ml.

Pharmaceutical compositions for use in the disclosed methods may be manufactured in conventional manner. In one embodiment, the pharmaceutical composition is provided in lyophilized form. For immediate administration it is dissolved in a suitable aqueous carrier, for example sterile water for injection or sterile buffered physiological saline. A reconstituted lyophilisate is referred to as a "reconstituent". If it is considered desirable to make up a solution of larger volume for administration by infusion rather than a bolus injection, may be advantageous to incorporate human serum albumin or the patient's own heparinized blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution. Other formulations comprise ready-to-use liquid formulations.

Exemplary pharmaceutical composition comprising the anti-BAFFR antibody, such as ianalumab, are disclosed in WO 2012/076670 and WO 2013/186700, incorporated herein by reference. In one embodiment, the pharmaceutical composition is provided for administration typically by infusion or via a delivery device (e.g. a syringe) including a pharmaceutical composition of the invention (e.g., pre-filled syringe).

Combinations

While it is understood that the disclosed methods provide for the treatment of LN patients, the therapy is not necessarily a monotherapy. Indeed, if a patient is selected for the treatment with an anti-BAFFR antibody, such as ianalumab, then the anti-BAFFR antibody, such as ianalumab, may be administered in accordance with the methods of the disclosure either alone or in combination with other agents and therapies for treating LN patients, e.g., in combination with at least one additional LN treatment, e.g. standard of care (SoC) treatment.

Various therapies may be beneficially combined with the disclosed anti-BAFFR antibodies, such as ianalumab, during treatment of LN. Non-limiting examples of LN agents used in systemic treatment with the disclosed anti-BAFFR antibodies, such as ianalumab, include IL-17 antagonists (ixekizumab, brodalumab, CJM112), steroids (e.g., corticosteroids, e.g., glucocorticoids, e.g., prednisolone, prednisone, methylprednisolone, etc.), e.g., mycophenolate mofetil (MMF), cyclosporine A, rituximab, ocrelizumab, abatacept, azathioprine (AZA), calcineurin inhibitors, cyclosporine A, tacrolimus, cyclophosphamide (CYC), mycophenolic acid (MPA) (including salts thereof), voclosporin, belimumab, ustekinumab, iguratimod, anifrolumab, B1655064, CFZ533, and combination thereof. Preferred LN agents for use in the disclosed kits, methods, and uses with the anti-BAFFR antibodies, such as ianalumab, are corticosteroids (e.g., glucocorticoids, e.g., methylprednisolone, prednisolone, prednisone), mycophenolate mofetil (MMF), mycophenolic acid (MPA) (including salts thereof) (collectively "MPA"), cyclophosphamide (CYC), and combinations thereof.

A skilled artisan will be able to discern the appropriate dosages of the above LN agents for co-delivery with the disclosed anti-BAFFR antibodies, such as ianalumab. See, e.g., Hahn et al. (2012) Arthritis Care Res (Hoboken) 64(6): 797-808.

An anti-BAFFR antibody, such as ianalumab, is conveniently administered parenterally, e.g., intravenously (e.g., into the antecubital or other peripheral vein), intramuscularly, or subcutaneously. The duration of intravenous (IV) therapy using a pharmaceutical composition of the present disclosure will vary, depending on the severity of the disease being treated and the condition and personal response of each individual patient. Also contemplated is subcutaneous (SC) therapy using a pharmaceutical composition of the present disclosure. The health care provider will decide on the appropriate duration of IV or SC therapy and the timing of administration of the therapy, using the pharmaceutical composition of the present disclosure.

In preferred embodiments, anti-BAFFR antibody, such as ianalumab, is administered via the subcutaneous (SC) route.

The anti-BAFFR antibody, e.g. ianalumab, may be administered to the patient SC, e.g., at about 150 mg-about 300 mg (e.g., about 150 mg, about 300 mg) monthly (every 4 weeks).

In some embodiments, it is contemplated that the anti-BAFFR antibody, e.g. ianalumab, may be administered to the patient intravenously (IV) at a dose of about 2 mg/kg-about 9 mg/kg (preferably about 3 mg/kg) every 4 weeks (monthly).

It will be understood that dose escalation may be required for certain patients, e.g., LN patients that display inadequate response (e.g., as measured by any of the LN scoring systems disclosed herein, e.g., CRR, PRR, estimated glomerular filtration rate (eGFR), 24-hour urinary protein to creatinine ratio, Functional Assessment of Chronic Illness Therapy—Fatigue (FACIT-Fatigue©), Short Form Health Survey (SF-36 Physical Component Summary (PCS), Lupus Quality of Life (LupusQoL), etc.) to treatment with the anti-BAFFR antibody, e.g. ianalumab, by week 10, week 12, week 14, week 16, week 18, week 20, week 22, week 24, week 48, week 52, or week 104 of treatment. Thus, SC dosages of ianalumab may be greater than about 150 mg-about 300 mg SC, e.g., about 200 mg, about 250 mg (in the case of an original 150 mg dose), about 350 mg, about 450 mg (in the case of an original 300 mg dose), etc.; similarly, IV dosages may be greater than about 2 mg/kg-about 9 mg/kg, e.g., about 2.5 mg/kg, about 3 mg/kg, 4 mg/kg, about 5 mg/kg, about 6 mg/kg (e.g., in the case of an original 2 mg/kg dose), about 9.5 mg/kg, 10 mg/kg, 11 mg/kg, 12 mg/kg (in the case of an original 9 mg/kg mg dose), etc.

Similarly, more frequent dosing may be used during the treatment with the anti-BAFFR antibody, e.g. ianalumab. These patients may be switched to more frequent administration (rather than increased dose), e.g., switched from administration of the anti-BAFFR antibody, e.g. ianalumab, every 4 weeks (monthly; Q4w) to administration every two weeks (Q2w) or every week (Q1w). This switch may be done as determined necessary by a physician, e.g., at week 10, week 12, week 14, week 16, week 18, week 20, week 22, week 24, week 48, week 52, or week 104 of treatment.

It will also be understood that dose reduction may also be used for certain patients, e.g., LP (e.g., CLP, MLP, LLP) patients that display a particularly robust treatment response, or an adverse event/response to treatment with the anti-BAFFR antibody, e.g. ianalumab. Thus, dosages of the anti-BAFFR antibody, e.g. ianalumab, may be lowered to less than about 150 mg-about 300 mg SC, e.g., about 250 mg, about 200 mg, about 150 mg (in the case of an original 300 mg dose); about 100 mg, about 50 mg (in the case of an original 150 mg dose), etc. Similarly, IV dosages may be lowered to less than about 8 mg/kg, e.g., about 7 mg/kg, 5 mg/kg, 4 mg/kg, 3 mg/kg, 2 mg/kg, 1 mg/kg, etc.

In some embodiments, the anti-BAFFR antibody, e.g. ianalumab may be administered to the patient at an initial dose of 300 mg or 150 mg delivered SC, and the dose is then escalated to about 450 mg (in the case of an original 300 mg dose) or about 300 mg (in the case of an original 150 mg dose) if needed, as determined by a physician.

Similarly, less frequent dosing may be used, e.g., a patient having a particularly robust treatment response, or an adverse event/response to treatment with the anti-BAFFR antibody, e.g. ianalumab. These patients may be switched to less frequent administration (rather than decreased dose), e.g., switched from administration of the anti-BAFFR antibody, e.g. ianalumab, every 4 weeks (monthly; Q4w) to administration every six weeks (Q6w) or eight weeks (Q8w). This switch may be done as determined necessary by a physician, e.g., at week 10, week 12, week 14, week 16, week 18, week 20, week 22, week 24, week 48, week 52, or week 104 of treatment.

As used herein, 'fixed dose' refers to a flat dose, i.e., a dose that is unchanged regardless of a patient's characteristics. Thus, a fixed dose differs from a variable dose, such as a body-surface area-based dose or a weight-based dose (typically given as mg/kg). In some embodiments of the disclosed methods, uses, pharmaceutical compositions, kits, etc., the LN patient is administered fixed doses of the anti-BAFFR antibody, e.g., fixed doses of ianalumab, e.g., fixed doses of about 75 mg-about 450 mg ianalumab, e.g., about 75 mg, about 150 mg, about 300 mg, about 400 mg or about 450 mg ianalumab. Alternatively, in some embodiments, the patient is administered a weight-based dose, e.g., a dose given in mg based on patient weight in kg (mg/kg).

As used herein, the phrase "formulated at a dosage to allow [route of administration] delivery of [a designated dose]" is used to mean that a given pharmaceutical composition can be used to provide a desired dose of an anti-BAFFR antibody, e.g. ianalumab, via a designated route of administration (e.g., SC or IV). As an example, if a desired SC dose is 300 mg, then a clinician may use 2 ml of an anti-BAFFR antibody, e.g. ianalumab, formulation having a concentration of 150 mg/ml, 1 ml of an anti-BAFFR antibody, e.g. ianalumab formulation having a concentration of 300 mg/ml, 0.5 ml of an anti-BAFFR antibody, e.g.

ianalumab formulation having a concentration of 600 mg/ml, etc. In each such case, these anti-BAFFR antibody, e.g. ianalumab, formulations are at a concentration high enough to allow subcutaneous delivery of the anti-BAFFR antibody. Subcutaneous delivery typically requires delivery of volumes of less than or equal to about 2 ml, preferably a volume of about 1 ml or less. Preferred formulations are ready-to-use liquid pharmaceutical compositions comprising about 50 mg/mL to about 150 mg/mL ianalumab, about 10 mM to about 30 mM histidine, about 200 mM to about 225 mM sucrose, about 0.02% to about 0.05% polysorbate 20, preferably having a pH of about 6.0 to about 6.5.

As used herein, the phrase “container having a sufficient amount of the anti-BAFFR antibody, e.g. ianalumab to allow delivery of [a designated dose]” is used to mean that a given container (e.g., vial, pen, syringe) has disposed therein a volume of anti-BAFFR antibody, e.g. ianalumab (e.g., as part of a pharmaceutical composition) that can be used to provide a desired dose. As an example, if a desired dose is 300 mg, then a clinician may use 2 mL from a container that contains anti-BAFFR antibody, e.g. ianalumab, formulation with a concentration of 150 mg/mL, 1 mL from a container that contains an anti-BAFFR antibody, e.g. ianalumab formulation with a concentration of 300 mg/mL, 0.5 mL from a container contains an anti-BAFFR antibody, e.g. ianalumab formulation with a concentration of 600 mg/ml, etc. In each such case, these containers have a sufficient amount of the anti-BAFFR antibody, e.g. ianalumab to allow delivery of the desired 300 mg dose.

In some embodiments of the disclosed uses, methods, and kits, the dose of the anti-BAFFR antibody, e.g. ianalumab is about 300 mg, the anti-BAFFR antibody, e.g. ianalumab is comprised in a liquid pharmaceutical formulation at a concentration of 150 mg/ml, and 2 ml of the pharmaceutical formulation is disposed within two pre-filled syringes, injection pens, or autoinjectors, each having 1 ml of the pharmaceutical formulation. In this case, the patient receives two injections of 1 ml each, for a total dose of 300 mg, during each administration. In some embodiments, the dose of the anti-BAFFR antibody, e.g. ianalumab is about 300 mg, the anti-BAFFR antibody, e.g. ianalumab is comprised in a liquid pharmaceutical formulation at a concentration of 150 mg/ml, and 2 ml of the pharmaceutical formulation is disposed within an autoinjector or PFS. In this case, the patient receives one injection of 2 ml, for a total dose of 300 mg, during each administration. In methods employing one injection of 2 ml (e.g., via a single PFS or autoinjector) (i.e., a “single-dose preparation”), the drug exposure (AUC) and maximal concentration (Cmax) is equivalent (similar to, i.e., within the range of acceptable variation according to US FDA standards) to methods employing two injections of 1 ml (e.g., via two PFSs or two AIs) (i.e., a “multiple-dose preparation”).

Accordingly, disclosed herein are methods of treating LN, comprising subcutaneously (SC) administering to a patient in need thereof a dose of about 150 mg-about 300 mg of an anti-BAFFR antibody, e.g. ianalumab monthly (every 4 weeks).

Disclosed herein are methods of treating LN, comprising subcutaneously (SC) administering to a patient in need thereof a dose of about 150 mg-about 300 mg (e.g., about 150 mg, about 300 mg) of an anti-BAFFR antibody, e.g. ianalumab monthly (every 4 weeks). Also disclosed herein is an anti-BAFFR antibody, e.g. ianalumab, for use in the manufacture of a medicament for treating LN, which is to be subcutaneously (SC) administered to a patient in need thereof at a dose of about 150 mg to about 300 mg (e.g., about 150 mg, about 300 mg) of the anti-BAFFR antibody, e.g. ianalumab monthly (every 4 weeks).

Disclosed herein are methods of treating LN, comprising subcutaneously (SC) administering to a patient in need thereof a dose of about 150 mg-about 300 mg of an anti-BAFFR antibody, e.g. ianalumab SC at a dose of about 150 mg-about 300 mg every 2 weeks.

In preferred embodiments of the disclosed methods, uses and kits, the dose of the anti-BAFFR antibody, e.g. ianalumab, is about 150 mg or about 300 mg.

In preferred embodiments of the disclosed methods, uses and kits, the patient achieves a complete renal response (CRR) by week 52 of treatment, a partial renal response (PPR) by week 52 of treatment, improvement in UPCR by week 52 of treatment, improvement in eGFR by week 52 of treatment, steroid reduction (e.g., to a dose of <11 mg daily) by week 52 of treatment, inactive urinary sediments (no cellular casts) by week 52 of treatment, improvement in FACIT-F fatigue score by week 52 of treatment, or any combination thereof.

In preferred embodiments of the disclosed methods, uses and kits, prior to treatment with the anti-BAFFR antibody, e.g. ianalumab, the patient was administered mycophenolic acid (MPA) or cyclophosphamide (CYC), and, optionally at least one steroid.

In preferred embodiments of the disclosed methods, uses and kits, prior to treatment with the anti-BAFFR antibody, e.g. ianalumab, the LN was inadequately controlled by the prior treatment with MPA or CYC, and, optionally the at least one steroid.

In preferred embodiments of the disclosed methods, uses and kits, during treatment with the anti-BAFFR antibody, e.g. ianalumab, the patient is concomitantly administered MPA or CYC, and, optionally at least one steroid.

In preferred embodiments of the disclosed methods, uses and kits, during treatment with the anti-BAFFR antibody, e.g. ianalumab, the dose of MPA or CYC administered to the patient is reduced, and wherein the patient does not experience a flare as a result of said reduction.

In preferred embodiments of the disclosed methods, uses and kits, during treatment with the anti-BAFFR antibody, e.g. ianalumab, the dose of the at least one steroid administered to the patient is reduced using a taper regimen, and wherein the patient does not experience a flare as a result of said reduction.

In preferred embodiments of the disclosed methods, uses and kits, the patient has active LN.

In preferred embodiments of the disclosed methods, uses and kits, the patient has International Society of Nephrology/Renal Pathology Society (ISN/RPS) Class III or IV LN.

In preferred embodiments of the disclosed methods, uses and kits, the ISN/RPS Class III IN is not Class III(C).

In preferred embodiments of the disclosed methods, uses and kits, the ISN/RPS Class IV LN is not Class IV-S(C) or IV-G(C).

In preferred embodiments of the disclosed methods, uses and kits, the patient has features of ISN/RPS Class V LN.

In preferred embodiments of the disclosed methods, uses and kits, the patient is additionally administered at least one LN agent selected from the group consisting of rituximab, ocrelizumab, abatacept, azathioprine, a calcineurin inhibitor, cyclosporine A, tacrolimus, cyclophosphamide, mycophenolic acid, voclosporin, belimumab, ustekinumab, iguratimod, anifrolumab, B1655064, CFZ533, and combinations thereof.

In preferred embodiments of the disclosed methods, uses and kits, the patient is an adult.

In preferred embodiments of the disclosed methods, uses and kits, the anti-BAFFR antibody, e.g. ianalumab, is disposed in a pharmaceutical formulation, wherein said pharmaceutical formulation further comprises a buffer and a stabilizer.

In preferred embodiments of the disclosed methods, uses and kits, the pharmaceutical formulation is a liquid pharmaceutical formulation.

In preferred embodiments of the disclosed methods, uses and kits, the pharmaceutical formulation is a lyophilized pharmaceutical formulation.

In preferred embodiments of the disclosed methods, uses and kits, the pharmaceutical formulation is disposed within at least one pre-filled syringe, at least one vial, at least one injection pen, or at least one autoinjector.

In preferred embodiments of the disclosed methods, uses and kits, the at least one pre-filled syringe, at least one vial, at least one injection pen, or at least one autoinjector is disposed within a kit, and wherein said kit further comprises instructions for use.

In preferred embodiments of the disclosed methods, uses and kits, the dose of the anti-BAFFR antibody, e.g. ianalumab, is 300 mg, which is administered to the patient as a single subcutaneous administration in a total volume of 2 milliliters (mL) from a formulation comprising 150 mg/ml of the anti-BAFFR antibody, e.g. ianalumab, wherein the pharmacological exposure of the patient to the anti-BAFFR antibody, e.g. ianalumab, is equivalent to the pharmacological exposure of the patient to the anti-BAFFR antibody, e.g. ianalumab, using two separate subcutaneous administrations of a total volume of 1 ml each of the same formulation.

In preferred embodiments of the disclosed methods, uses and kits, the dose of the anti-BAFFR antibody, e.g. ianalumab, is administered to the patient is 300 mg, which is administered as two separate subcutaneous administrations in a volume of 1 mL each from a formulation comprising 150 mg/ml of the anti-BAFFR antibody, e.g. ianalumab.

In preferred embodiments of the disclosure, when said method is used to treat a population of patients having LN, at least 50% of said patients achieve a daily steroid dose of <10 mg/day following a steroid tapering regimen during treatment with the anti-BAFFR antibody, e.g. ianalumab.

In preferred embodiments of the disclosure, when said method is used to treat a population of patients having LN, at least 50% of said patients achieve a daily steroid dose of <5 mg/day following a steroid tapering regimen during treatment with the anti-BAFFR antibody, e.g. ianalumab.

In preferred embodiments of the disclosure, when said method is used to treat a population of patients having LN, at least 15% of said patients achieve a CRR following 52 weeks of treatment with the anti-BAFFR antibody, e.g. ianalumab.

In preferred embodiments of the disclosure, when said method is used to treat a population of patients having LN, at least 20% of said patients achieve a CRR following 52 weeks of treatment with the anti-BAFFR antibody, e.g. ianalumab.

In preferred embodiments of the disclosed methods, uses and kits, the patient achieves an improvement in UPCR of >75% by week 52.

In preferred embodiments of the disclosed methods, uses and kits, the patient is treated with the anti-BAFFR antibody, e.g. ianalumab, for at least one year.

In preferred embodiments of the disclosure, the anti-BAFFR antibody is ianalumab.

Disclosed herein are methods of treating an adult patient with active LN who previously had an inadequate response to prior treatment with standard-of-care LN therapy, comprising administering a dose of about 300 mg ianalumab subcutaneously to said patient every four weeks (monthly), and further comprising concomitantly administering to said patient standard-of-care LN therapy, wherein said patient has ISN/RPS Class III or IV LN.

Disclosed herein are methods of treating a patient (e.g., an adult patient) with active lupus nephritis, comprising administering a dose of about 300 mg ianalumab subcutaneously to said patient every four weeks (monthly), and further comprising concomitantly administering to said patient standard-of-care LN therapy.

Disclosed herein are methods of treating a patient (e.g., an adult patient) with active lupus nephritis, comprising administering a dose of about 300 mg ianalumab subcutaneously to said patient every four weeks (monthly), and further comprising concomitantly administering to said patient standard-of-care LN therapy, wherein said patient has ISN/RPS Class III or IV LN.

In some embodiments, the standard-of-care LN therapy comprises treatment with MPA or cyclophosphamide (CYC) and, optionally, a steroid.

Disclosed herein are methods of treating a patient (e.g., an adult patient) with active lupus nephritis, comprising administering a dose of about 300 mg ianalumab subcutaneously to said patient every four weeks (monthly).

Disclosed herein are methods of treating a patient (e.g., an adult patient) having LN, comprising intravenously (IV) administering to the patient a dose of about 3 mg/kg ianalumab, every four weeks (monthly).

Disclosed herein are methods of treating a patient (e.g., an adult patient) having active lupus nephritis, comprising intravenously (IV) administering to the patient a dose of about 3 mg/kg to about 9 mg/kg (preferably about 3 mg/kg) ianalumab every four weeks.

Kits

The disclosure also encompasses kits for treating LN. Such kits comprise an anti-BAFFR antibody, e.g. ianalumab, (e.g., in liquid or lyophilized form) or a pharmaceutical composition comprising the anti-BAFFR antibody (described supra). Additionally, such kits may comprise means for administering the anti-BAFFR antibody, e.g. ianalumab, (e.g., an autoinjector, a syringe and vial, a prefilled syringe, a prefilled pen) and instructions for use. These kits may contain additional therapeutic HS agents (described supra) for treating LN, e.g., for delivery in combination with the enclosed anti-BAFFR antibody, e.g. ianalumab. Such kits may also comprise instructions for administration of the anti-BAFFR antibody, e.g. ianalumab, to treat the LN patient. Such instructions may provide the dose (e.g., 3 mg/kg, 6 mg/kg, 150 mg, 300 mg), route of administration (e.g., IV, SC), and dosing regimen (e.g., weekly, monthly, weekly and then monthly, weekly and then every other week, etc.) for use with the enclosed anti-BAFFR antibody, e.g. ianalumab.

The phrase "means for administering" is used to indicate any available implement for systemically administering a drug to a patient, including, but not limited to, a pre-filled syringe, a vial and syringe, an injection pen, an autoinjector, an IV drip and bag, a pump, etc. With such items, a patient may self-administer the drug (i.e., administer the drug without the assistance of a physician) or a medical practitioner may administer the drug. In some embodiments, a total dose of 300 mg is to be delivered in a total volume of 2 ml, which is disposed in two PFSs or autoinjectors, each PFS or autoinjector containing a volume of 1 ml having 150 mg/ml of the anti-BAFFR antibody, e.g. ianalumab. In this case, the patient receives two 1 ml injections (a multi-dose preparation). In preferred embodiments, a total dose of 300 mg is to be delivered in a total volume of 2 ml having 150 mg/ml of the anti-BAFFR antibody, e.g. ianalumab, which is disposed in a single PFS or autoinjector. In this case, the patient receives one 2 ml injection (a single dose preparation).

Disclosed herein are kits for use treating a patient having LN, comprising an anti-BAFFR antibody, e.g. ianalumab, and means for administering the anti-BAFFR antibody, e.g. ianalumab, to the LN patient. In some embodiments, the kit further comprises instructions for administration of the anti-BAFFR antibody, e.g. ianalumab, wherein the instructions indicate that the anti-BAFFR antibody, e.g. ianalumab, is to be administered to the patient SC at a dose of about 150 mg-about 300 mg (e.g., about 150 mg, about 300 mg) every four weeks. In some embodiments, the kit further comprises instructions for administration of the anti-BAFFR antibody, e.g. ianalumab, is to be administered to the patient intravenously (IV) at a dose of about 3 mg/kg-about 9 mg/kg (preferably about 3 mg/kg) every 4 weeks (monthly).

General

In most preferred embodiments of the disclosed methods, kits, or uses, the anti-BAFFR antibody is ianalumab.

In preferred embodiments of the disclosed methods, kits, or uses, the dose size is flat (also referred to as a "fixed" dose, which differs from weight-based or body surface area-based dosing), the dose is 300 mg, the route of administration is SC, and the regimen is administration every four weeks.

In other embodiments of the disclosed methods, kits, or uses, the dose size is weight-based, the dose is 3 mg/kg, the route of administration is IV, and the regimen is administration every four weeks.

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural references unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference. The following Examples are presented in order to more fully illustrate the preferred embodiments of the disclosure. These examples should in no way be construed as limiting the scope of the disclosed subject matter, as defined by the appended claims.

EXAMPLES

Example 1: A Randomized, Double-Blind, Parallel Group, Placebo-Controlled, Multicenter Phase 3 Trial to Evaluate the Efficacy, Safety and Tolerability of Ianalumab on Top of Standard-of Care Therapy in Patients with Active Lupus Nephritis Study Purpose The purpose of this trial is to evaluate the efficacy and safety of subcutaneous (SC) ianalumab 300 mg compared to placebo, in combination with standard of care therapy (SoC), in subjects with active lupus nephritis (ISN/RPS Class III or IV, with or without co-existing class V features, using the 2003 International Society for Nephrology (ISN)/Renal Pathology Society (RPS) criteria).

Background SoC will consist of induction therapy with mycophenolic acid (MPA) (which refers to Mycophenolate mofetil (MMF) (Cellcept® or generic equivalent), or enteric-coated MPA sodium (Myfortic® or generic equivalent) at equivalent doses (oral), or Cyclophosphamide (CYC) (i.v.), followed by maintenance therapy with MPA. In addition, all subjects will receive i.v. and/or oral corticosteroids.

This is a double-blind, randomized, placebo-controlled, multi-center two-arm study, evaluating a dose of 300 mg ianalumab administered s.c. once monthly against placebo, in patients with active LN receiving standard-of-care treatment.

The study consists of the following periods:

Screening period (up to 6 weeks): Patients fulfilling ACR/EULAR SLE classification and active LN criteria (including renal biopsy evaluation) will be assessed for eligibility.

Blinded treatment period #1 (18 months): At baseline visit, eligible patients will be randomly assigned in a 1:1 ratio to receive once-monthly either ianalumab 300 mg or placebo. A total of 18 once-monthly administrations of the study treatment will be performed over 17 months on top of SoC background therapy. The study treatment will be given as two subcutaneous (s.c.) injections of 1 mL each using a pre-filled syringe (PFS).

Blinded treatment period #2 (18 months): At Month 18 visit, all patients who have completed the first blinded treatment period will be randomly re-assigned in a 1:1 ratio to receive either once-monthly or once quarterly ianalumab 300 mg. Starting at Month 18, all patients will receive ianalumab 300 mg s.c. monthly or ianalumab 300 mg s.c. quarterly, with last dose at Month 36.

Safety follow up: Patients who discontinue the blinded period #1 (prior to Month 18) or blinded treatment period #2 (prior to Month 36) study treatment prematurely or who at Month 36 complete both treatment periods will move to the post-treatment follow-up.

Patients will be followed for at least 5 months (mandatory follow up) or longer (conditional follow up), until B-cell recovery or up to 2 years after the last dose of the study treatment.

Rationale for Dose and Regimen

The dose regimen for this study will be 300 mg s.c. ianalumab once monthly for the treatment period of 18 months. Our data strongly suggests that ianalumab operates at the plateau of the dose-exposure-response curve in the autoimmune diseases for which it has been tested, which is one of the reasons to select this dose level in LN as well.

Pharmacokinetic simulation results suggest that patients weighing down to 35 kg would not have their ianalumab exposure exceeding twice the exposure of patients weighing 70 kg.

Nevertheless, it has to be noted that due to kidney damage, proteinuria is commonly observed in patients with LN. The effect of renal impairment on the PK of biologics is dependent on the ability of the compound to undergo glomerular filtration, which is largely driven by molecular weight (MW). In biologics with MW greater than 69 kDa, renal clearance usually plays a minimal role in the elimination (Meibohm 2012). Ianalumab has a MW of 147 kDa, and thus it is not expected that renal impairment will alter the PK of ianalumab.

Ianalumab 300 mg q4w provides rapid and sustained B cell depletion, suggestive of sustained BAFF-R blockade based on biomarker results. Ianalumab 300 mg q4w has a favorable safety profile; there are no dose-related safety observations other than mostly mild, local injection site reactions.

Ianalumab 300 mg given every 3 months (q12w, quarterly) is expected to maintain depletion of circulating B cells and associated clinical effects.

Example 2: A Placebo-Controlled, Patient and Investigator Blinded, Randomized Parallel Cohort Study to Assess Pharmacodynamics, Pharmacokinetics, Safety, Tolerability and Efficacy of VAY736 in Patients with Systemic Lupus Erythematosus (SLE)

This is a double-blind, randomized, placebo-controlled, multi-center two-arm study, evaluating a dose of 300 mg ianalumab administered s.c. once monthly against placebo, in patients with SLE receiving standard-of-care treatment.

Results: The proportion of study patients who achieved the composite primary endpoint at Week 28 of SRI-4 under sustained prednisolone reduction ≤5 mg/d was 42% greater for ianalumab than for placebo. Ianalumab also was better than placebo for the incidence of moderate or severe flares (45% vs 73%, respectively) and time-to-first flare (median not reached vs 11.9 weeks, respectively). At Week 28 the differences between ianalumab and placebo were 50% for proportion of patients achieving SRI-4 response, 34% for reduced corticosteroid use, 43% for the primary combined endpoint of these two outcomes, 20% for Lupus Low Disease Activity State (LLDAS) and 31% for BILAG-based Combined Lupus Assessment (BICLA). Ianalumab was well tolerated without any new safety signals detected during the blinded 28-week treatment period as well as during the open-label treatment period (Week 28 to Week 52) and subsequent safety follow up period.

SPECIFIC EMBODIMENTS, CITATION OF REFERENCES

While various specific embodiments have been illustrated and described, it will be appreciated that various changes can be made without departing from the spirit and scope of the disclosure(s). The present disclosure is exemplified by the numbered embodiments set forth below.

1. An anti-BAFFR antibody or a binding fragment thereof for use in the treatment of LN in a subject in need thereof, wherein the anti-BAFFR antibody or binding fragment thereof is to be administered at a therapeutically effective dose.

2. The anti-BAFFR antibody or a binding fragment thereof for use according to embodiment 1, wherein the anti-BAFFR antibody or binding fragment thereof comprises CDR-H1, CDR-H2, and CDR-H3 having the amino acid sequences of SEQ ID NO:3, SEQ ID NO:4, and SEQ ID NO:5, and CDR-L1, CDR-L2, and CDR-L3 having the amino acid sequences of SEQ ID NO:6, SEQ ID NO:7, and SEQ ID NO:8, respectively.

3. The anti-BAFFR antibody or a binding fragment thereof for use according to embodiment 1 or embodiment 2, wherein the anti-BAFFR antibody or binding fragment thereof comprises a heavy chain variable region having the amino acid sequence of SEQ ID NO: 1 and a light chain variable region having the amino acid sequence of SEQ ID NO: 2

4. The anti-BAFFR antibody or a binding fragment thereof for use according to any one of embodiments 1 to 3, wherein the anti-BAFFR antibody or binding fragment thereof is ianalumab or a binding fragment thereof.

5. The anti-BAFFR antibody or a binding fragment thereof for use according to any one of embodiments 1 to 4, wherein the anti-BAFFR antibody or binding fragment thereof is to be administered at a dose of 50 mg to 300 mg.

6. The anti-BAFFR antibody or a binding fragment thereof for use according to embodiment 5, wherein the anti-BAFFR antibody or binding fragment thereof is to be administered at a dose of 150 mg to 300 mg.

7. The anti-BAFFR antibody or a binding fragment thereof for use according to embodiment 5, wherein the anti-BAFFR antibody or binding fragment thereof is to be administered at a dose of 150 mg.

8. The anti-BAFFR antibody or a binding fragment thereof for use according to embodiment 5, wherein the anti-BAFFR antibody or binding fragment thereof is to be administered at a dose of 300 mg.

9. The anti-BAFFR antibody or a binding fragment thereof for use according to embodiments 1-4, wherein the anti-BAFFR antibody or binding fragment thereof is to be administered at a dose of from about 1 mg/kg to about 10 mg/kg.

10. The anti-BAFFR antibody or a binding fragment thereof for use according to embodiment 9, wherein the anti-BAFFR antibody or binding fragment thereof is to be administered at a dose of 3 mg/kg.

11. The anti-BAFFR antibody or a binding fragment thereof for use according to embodiment 9, wherein the anti-BAFFR antibody or binding fragment thereof is to be administered at a dose of 6 mg/kg.

12. The anti-BAFFR antibody or a binding fragment thereof for use according to embodiment 9, wherein the anti-BAFFR antibody or binding fragment thereof is to be administered at a dose of 9 mg/kg.

13. The anti-BAFFR antibody or a binding fragment thereof for use according to any one of embodiments 1 to 12, wherein the anti-BAFFR antibody or binding fragment thereof is to be administered to a subject in need thereof once every two weeks (+/−3 days).

14. The anti-BAFFR antibody or a binding fragment thereof for use according to any one of embodiments 1 to 13, wherein the anti-BAFFR antibody or binding fragment thereof is to be administered to a subject in need thereof once every 4 weeks (+/−3 days).

15. The anti-BAFFR antibody or a binding fragment thereof for use according to any one of embodiments 9 to 12, wherein the anti-BAFFR antibody or binding fragment thereof is to be administered intravenously to a subject in need thereof.

16. The anti-BAFFR antibody or a binding fragment thereof for use according to any one of embodiments 5 to 8, wherein the anti-BAFFR antibody or binding fragment thereof is to be administered subcutaneously to a subject in need thereof 17. The anti-BAFFR antibody or a binding fragment thereof for use according to any one of embodiments 1 to 16, wherein the anti-BAFFR antibody or binding fragment thereof is to be administered as monotherapy for the treatment of LN.

18. The anti-BAFFR antibody or a binding fragment thereof for use according to any one of embodiments 1 to 17, wherein the anti-BAFFR antibody or binding fragment thereof is to be administered in combination with one or more additional agents.

19. The anti-BAFFR antibody or a binding fragment thereof for use according to any one of embodiments 1 to 18, wherein prior to treatment with anti-BAFFR antibody or a binding fragment thereof, the patient was administered mycophenolic acid (MPA) or cyclophosphamide (CYC), and, optionally at least one steroid.

20. The anti-BAFFR antibody or a binding fragment thereof for use according to any one of embodiments 1 to 19, wherein prior to treatment with anti-BAFFR antibody or a binding fragment thereof, the LN was inadequately controlled by the prior treatment with MPA or CYC, and, optionally the at least one steroid.

21. The anti-BAFFR antibody or a binding fragment thereof for use according to any one of embodiments 1 to 18, wherein during treatment with anti-BAFFR antibody or a binding fragment thereof, the patient is concomitantly administered MPA or CYC, and, optionally at least one steroid.

22. The anti-BAFFR antibody or a binding fragment thereof for use according to embodiment 21, wherein during treatment with the anti-BAFFR antibody or a binding fragment, the dose of MPA or CYC administered to the patient is reduced, and wherein the patient does not experience a flare as a result of said reduction.

23. The anti-BAFFR antibody or a binding fragment thereof for use according to embodiment 21 or 22, wherein during treatment with the anti-BAFFR antibody or a binding fragment thereof, the dose of the at least one steroid administered to the patient is reduced using a taper regimen, and wherein the patient does not experience a flare as a result of said reduction.

24. The anti-BAFFR antibody or a binding fragment thereof for use according to any one of embodiments 1 to 23, wherein the patient does not have concomitant plaque-type psoriasis.

25. The anti-BAFFR antibody or a binding fragment thereof for use according to any one of the above embodiments, wherein the patient has active LN.

26. The anti-BAFFR antibody or a binding fragment thereof for use according to any one of the above embodiments, wherein the patient has International Society of Nephrology/Renal Pathology Society (ISN/RPS) Class III or IV LN.

27. The anti-BAFFR antibody or a binding fragment thereof for use according to embodiment 26, wherein the ISN/RPS Class III IN is not Class III(C).

28. The anti-BAFFR antibody or a binding fragment thereof for use according to embodiment 26 wherein the ISN/RPS Class IV LN is not Class IV-S(C) or IV-G(C).

29. The anti-BAFFR antibody or a binding fragment thereof for use according to any one of the above embodiments, wherein the patient has features of ISN/RPS Class V LN.

30. The anti-BAFFR antibody or a binding fragment thereof for use according to any one of the above embodiments, wherein said patient achieves a complete renal response (CRR) after one year of treatment 31. The anti-BAFFR antibody or a binding fragment thereof for use according to any one of the above embodiments, wherein said patient achieves a partial renal response (PRR) after one year of treatment.

32. The anti-BAFFR antibody or a binding fragment thereof for use according to any one of the above embodiments, wherein the patient is additionally administered at least one LN agent selected from the group consisting of rituximab, ocrelizumab, abatacept, azathioprine, a calcineurin inhibitor, cyclosporine A, tacrolimus, cyclophosphamide, mycophenolic acid, voclosporin, belimumab, ustekinumab, iguratimod, anifrolumab, B1655064, CFZ533, and combinations thereof.

33. The anti-BAFFR antibody or a binding fragment thereof for use according to any one of the above embodiments, wherein the patient is an adult.

34. The anti-BAFFR antibody or a binding fragment thereof for use according to any one of the above embodiments, wherein anti-BAFFR antibody or a binding fragment thereof is disposed in a pharmaceutical formulation, wherein said pharmaceutical formulation further comprises a buffer and a stabilizer.

35. The anti-BAFFR antibody or a binding fragment thereof for use according to embodiment 34, wherein the pharmaceutical formulation is a liquid pharmaceutical formulation.

36. The anti-BAFFR antibody or a binding fragment thereof for use according to embodiment 34, wherein the pharmaceutical formulation is a lyophilized pharmaceutical formulation.

37. The anti-BAFFR antibody or a binding fragment thereof for use according to embodiments 34 to 36, wherein the pharmaceutical formulation is disposed within at least one pre-filled syringe, at least one vial, at least one injection pen, or at least one autoinjector.

38. The anti-BAFFR antibody or a binding fragment thereof for use according to embodiments 37, wherein the at least one pre-filled syringe, at least one vial, at least one injection pen, or at least one autoinjector is disposed within a kit, and wherein said kit further comprises instructions for use.

39. The anti-BAFFR antibody or a binding fragment thereof for use according to any one of the above embodiments, wherein the dose of the anti-BAFFR antibody or a binding fragment is 300 mg, which is administered to the patient as a single subcutaneous administration in a total volume of 2 milliliters (mL) from a formulation comprising 150 mg/ml of the anti-BAFFR antibody or a binding fragment, wherein the pharmacological exposure of the patient to the anti-BAFFR antibody or a binding fragment is equivalent to the pharmacological exposure of the patient to the anti-BAFFR antibody or a binding fragment using two separate subcutaneous administrations of a total volume of 1 ml each of the same formulation.

40. The anti-BAFFR antibody or a binding fragment thereof for use according to any one of the above embodiments 1 to 38, wherein the dose of the anti-BAFFR antibody or a binding fragment thereof administered to the patient is 300 mg, which is administered as two separate subcutaneous administrations in a volume of 1 mL each from a formulation comprising 150 mg/ml of the anti-BAFFR antibody or a binding fragment thereof.

41. The anti-BAFFR antibody or a binding fragment thereof for use according to any one of the above embodiments 1 to 40, wherein anti-BAFFR antibody or a binding fragment thereof is a human monoclonal antibody.

42. The anti-BAFFR antibody or a binding fragment thereof for use according to any one of the above embodiments 1 to 41, wherein the anti-BAFFR antibody or a binding fragment thereof is of the IgG1/kappa isotype.

43. The anti-BAFFR antibody or a binding fragment thereof for use according to any one of the above embodiments 1 to 42 for use to treat a population of patients having LN, at least 50% of said patients achieve a daily steroid dose of <10 mg/day following a steroid tapering regimen during treatment with the anti-BAFFR antibody or a binding fragment thereof.

44. The anti-BAFFR antibody or a binding fragment thereof for use according to any one of the above embodiments, wherein, when said method is used to treat a population of patients having LN, at least 50% of said patients achieve a daily steroid dose of <5 mg/day following a steroid tapering regimen during treatment with anti-BAFFR antibody or a binding fragment thereof.

45. The anti-BAFFR antibody or a binding fragment thereof for use according to any one of the above embodiments, wherein, when said method is used to treat a population of patients having LN, at least 15% of said patients achieve a CRR following 52 weeks of treatment with the anti-BAFFR antibody or a binding fragment thereof.

46. The anti-BAFFR antibody or a binding fragment thereof for use according to any one of the above embodiments, wherein, when said method is used to treat a population of patients having LN, at least 20% of said patients achieve a CRR following 52 weeks of treatment with the anti-BAFFR antibody or a binding fragment thereof.

47. The anti-BAFFR antibody or a binding fragment thereof for use according to any one of the above embodiments, wherein the patient achieves an improvement in UPCR of >75% by week 52.

48. The anti-BAFFR antibody or a binding fragment thereof for use according to any one of the above embodiments, wherein the patient is treated with the anti-BAFFR antibody or a binding fragment thereof for at least one year.

49. The anti-BAFFR antibody or a binding fragment thereof for use according to any one of the above embodiments, wherein the anti-BAFFR antibody or a binding fragment thereof is ianalumab.

50. A method of treating an adult patient with active LN who previously had an inadequate response to prior treatment with standard-of-care LN therapy, comprising administering a dose of about 300 mg ianalumab subcutaneously to said patient every four weeks, and further comprising concomitantly administering to said patient standard-of-care LN therapy, wherein said patient has ISN/RPS Class III or IV LN.

51. A method of treating a patient (e.g., an adult patient) with active lupus nephritis, comprising administering a dose of about 300 mg ianalumab subcutaneously to said patient every four weeks, and further comprising concomitantly administering to said patient standard-of-care LN therapy.

52. A method of treating a patient (e.g., an adult patient) with active lupus nephritis, comprising administering a dose of about 300 mg ianalumab subcutaneously to said every four weeks, and further comprising concomitantly administering to said patient standard-of-care LN therapy, wherein said patient has ISN/RPS Class III or IV LN.

53. The method of any one of embodiments 50-52, wherein said standard-of-care LN therapy comprises treatment with MPA or cyclophosphamide (CYC) and, optionally, a steroid.

54. A method of treating a patient (e.g., an adult patient) with active lupus nephritis, comprising administering a dose of about 300 mg ianalumab subcutaneously to said patient every two weeks.

55. A method of treating a patient (e.g., an adult patient) having LN, comprising intravenously (IV) administering to the patient a dose of about 3 mg/kg ianalumab every four weeks.

56. A method of treating a patient (e.g., an adult patient) having active lupus nephritis, comprising intravenously (IV) administering to the patient a dose of about 3 mg/kg to about 9 mg/kg (preferably about 3 mg/kg) ianalumab every four weeks.

57. A method of treating a subject having LN, comprising administering therapeutically effective dose of an anti-BAFFR antibody or a binding fragment thereof to the subject.

58. The method of embodiment 57, wherein the anti-BAFFR antibody or binding fragment thereof comprises CDR-H1, CDR-H2, and CDR-H3 having the amino acid sequences of SEQ ID NO:3, SEQ ID NO:4, and SEQ ID NO:5, and CDR-L1, CDR-L2, and CDR-L3 having the amino acid sequences of SEQ ID NO:6, SEQ ID NO:7, and SEQ ID NO:8, respectively.

59. The of embodiment 57 or embodiment 58, wherein the anti-BAFFR antibody or binding fragment thereof comprises a heavy chain variable region having the amino acid sequence of SEQ ID NO: 1 and a light chain variable region having the amino acid sequence of SEQ ID NO: 2

60. The method of any one of embodiments 57 to 59, wherein the anti-BAFFR antibody or binding fragment thereof is ianalumab or a binding fragment thereof.

61. The method of any one of embodiments 57 to 60, wherein the anti-BAFFR antibody or binding fragment thereof is administered at a dose of 1 mg/kg to 10 mg/kg.

62. The method of embodiment 61, wherein the anti-BAFFR antibody or binding fragment thereof is administered at a dose of 3 mg/kg to 10 mg/kg.

63. The method of embodiment 61, wherein the anti-BAFFR antibody or binding fragment thereof is administered is administered at a dose of 1 mg/kg.

64. The method of embodiment 61, wherein the anti-BAFFR antibody or binding fragment thereof is administered at a dose of 3 mg/kg.

65. The method of embodiment 61, wherein the anti-BAFFR antibody or binding fragment thereof is administered at a dose of 6 mg/kg.

66. The method of embodiment 61, wherein the anti-BAFFR antibody or binding fragment thereof is administered, wherein the anti-BAFFR antibody or binding fragment thereof is administered at a dose of 9 mg/kg.

67. The method of any one of embodiments 50 to 63, wherein the anti-BAFFR antibody or binding fragment thereof is administered to the subject once every 4 weeks (+/−3 days).

68. The method of any one of embodiments 50 to 79, wherein the anti-BAFFR antibody or binding fragment thereof is administered intravenously to the subject.

69. The method of any one of embodiments 50 to 80, wherein the anti-BAFFR antibody or binding fragment thereof is administered as monotherapy for LN.

70. The method of any one of embodiments 50 to 80, wherein the anti-BAFFR antibody or binding fragment thereof is administered in combination with one or more additional LN agents disclosed herein.

71. Use of an anti-BAFFR antibody in the manufacture of a medicament for treating a subject having LN, optionally wherein the medicament is for administration in combination with one or more additional agents, optionally wherein the one or more additional agents are one or more additional LN agent selected from the group consisting of rituximab, ocrelizumab, abatacept, azathioprine, a calcineurin inhibitor, cyclosporine A, tacrolimus, cyclophosphamide, mycophenolic acid, voclosporin, belimumab, ustekinumab, iguratimod, anifrolumab, B1655064, CFZ533, and combinations thereof.

72. Use an additional agent in the manufacture of a medicament for treating a subject having LN, wherein the medicament is for administration in combination with an anti-BAFFR antibody or binding fragment thereof, optionally wherein the additional LN agent is an agent described in embodiment 71.

73. The use of embodiment 71 or embodiment 72, wherein the anti-BAFFR antibody or binding fragment thereof is an anti-BAFFR antibody or binding fragment thereof described in any one of embodiments 1 to 49.

74. The use of any one of embodiments 71 to 72, wherein the anti-BAFFR antibody and/or one or more additional agents are formulated for administration according to the method of any one of embodiments 50 to 70.

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there are any inconsistencies between the teachings of one or more of the references incorporated herein and the present disclosure, the teachings of the present specification are intended.

What is claimed is:

1. A method of treating lupus nephritis (LN) in a subject in need thereof by administering a therapeutically effective dose of an anti-BAFFR antibody to the subject, wherein the anti-BAFFR antibody comprises CDR-H1, CDR-H2, and CDR-H3 having the amino acid sequences of SEQ ID NO:3, SEQ ID NO:4, and SEQ ID NO:5, and CDR-L1, CDR-L2, and CDR-L3 having the amino acid sequences of SEQ ID NO:6, SEQ ID NO: 7, and SEQ ID NO:8, respectively.

2. The method of claim 1, wherein the anti-BAFFR antibody comprises a heavy chain variable region having the amino acid sequence of SEQ ID NO: 1 and a light chain variable region having the amino acid sequence of SEQ ID NO: 2.

3. The method of claim 1, wherein the anti-BAFFR antibody is ianalumab.

4. The method of claim 3, wherein the anti-BAFFR antibody is to be administered at a dose of 50 mg to 300 mg.

5. The method of claim 4, wherein the anti-BAFFR antibody is to be administered at a dose of 150 mg to 300 mg.

6. The method of claim 3, wherein the anti-BAFFR antibody is to be administered at a dose of 300 mg.

7. The method of claim 3, wherein the anti-BAFFR antibody is to be administered at a dose of 1 mg/kg to 10 mg/kg.

8. The method of claim 1, wherein during treatment with the anti-BAFFR antibody, a dose of at least one steroid administered to the subject is reduced using a taper regimen, and wherein the subject does not experience a flare as a result of said reduction.

9. The method of claim 1, wherein the dose of the anti-BAFFR antibody, administered to the patient is 300 mg, which is administered as two separate subcutaneous administrations in a volume of 1 mL each from a formulation comprising 150 mg/ml of the anti-BAFFR antibody.

10. The method of claim 1, wherein the anti-BAFFR antibody is administered to the subject once every 4 weeks.

11. The-method of claim 1, wherein the anti-BAFFR antibody is administered to the subject once every 12 weeks.

* * * * *

SEQUENCE LISTING

```
<160> NUMBER OF SEQ ID NOS: 15

<210> SEQ ID NO 1
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Ser Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser
        115                 120


<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Ile Ser Ser Ser
```

```
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Leu Tyr Ser Ser Pro
                85                  90                  95

Met Thr Phe Gly Gln Gly Thr Lys Val Glu Ile Lys
            100                 105


<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Asp Ser Val Ser Ser Asn Ser Ala Ala Trp Gly
1               5                   10


<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ile Tyr Tyr Arg Ser Lys Trp Tyr Asn Ser Tyr Ala Val Ser Val
1               5                   10                  15

Lys Ser


<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Asp Trp Val Pro Lys Ile Gly Val Phe Asp Ser
1               5                   10


<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Gln Phe Ile Ser Ser Ser Tyr Leu Ser
1               5                   10


<210> SEQ ID NO 7
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 7

Gly Ser Ser Ser Arg Ala Thr
1               5


<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Leu Tyr Ser Ser Pro Met Thr
1               5


<210> SEQ ID NO 9
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Ser Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240
```

```
Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450


<210> SEQ ID NO 10
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Ile Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Leu Tyr Ser Ser Pro
                85                  90                  95

Met Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
```

```
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 11
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

caggtgcagc tgcagcagag cggcccaggc ctggtcaagc cctctcagac cctgtcactg     60

acctgcgcca tttcaggcga cagcgtgagc agcaacagcg ccgcctgggg ctggatcagg    120

cagagccccg gtaggggcct ggaatggctg ggcaggatct actacaggtc caagtggtac    180

aacagctacg ccgtgagcgt gaagagcagg atcaccatca accctgacac cagcaagaac    240

cagttctcac tgcagctcaa cagcgtgacc cccgaggaca ccgccgtgta ctactgcgcc    300

agatacgact gggtgcccaa gatcggcgtg ttcgacagct ggggccaggg caccctggtg    360

accgtgtcaa gc                                                        372


<210> SEQ ID NO 12
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

gatatcgtgc tgacacagag ccccgccacc ctgagcctga gcccaggcga gagggccacc     60

ctgtcctgca gggccagcca gtttatcagc agcagctacc tgtcctggta tcagcagaag    120

cccggccagg cccctagact gctgatctac ggcagctcct ctcgggccac cggcgtgccc    180

gccaggttca gcggcagcgg ctccggcacc gacttcaccc tgacaatcag cagcctggag    240

cccgaggact tcgccgtgta ctactgccag cagctgtaca gctcacccat gaccttcggc    300

cagggcacca aggtggagat caag                                           324


<210> SEQ ID NO 13

<400> SEQUENCE: 13

000


<210> SEQ ID NO 14
<211> LENGTH: 1419
<212> TYPE: DNA
<213> ORGANISM: Artificial Sequence
<220> FEATURE:
<223> OTHER INFORMATION: Description of Artificial Sequence: Synthetic
```

polynucleotide

<400> SEQUENCE: 14
atggcctggg tgtggaccct gcccttcctg atggccgctg cccagtcagt gcaggcccag 60
gtgcagctgc agcagagcgg cccaggcctg gtcaagccct ctcagaccct gtcactgacc 120
tgcgccattt caggcgacag cgtgagcagc aacagcgccg cctggggctg gatcaggcag 180
agccccggta ggggcctgga atggctgggc aggatctact acaggtccaa gtggtacaac 240
agctacgccg tgagcgtgaa gagcaggatc accatcaacc ctgacaccag caagaaccag 300
ttctcactgc agctcaacag cgtgaccccc gaggacaccg ccgtgtacta ctgcgccaga 360
tacgactggg tgcccaagat cggcgtgttc gacagctggg gccagggcac cctggtgacc 420
gtgtcaagcg ccagcaccaa gggccccagc gtgttccccc tggcccccag cagcaagagc 480
accagcggcg gcacagccgc cctgggctgc ctggtgaagg actacttccc cgagcccgtg 540
accgtgtcct ggaacagcgg agccctgacc tccggcgtgc acaccttccc cgccgtgctg 600
cagagcagcg gcctgtacag cctgtccagc gtggtgacag tgcccagcag cagcctgggc 660
acccagacct acatctgcaa cgtgaaccac aagcccagca acaccaaggt ggacaagaga 720
gtggagccca agagctgcga caagacccac acctgccccc cctgcccagc cccagagctg 780
ctgggcggac cctccgtgtt cctgttcccc cccaagccca aggacaccct gatgatcagc 840
aggacccccg aggtgacctg cgtggtggtg gacgtgagcc acgaggaccc agaggtgaag 900
ttcaactggt acgtggacgg cgtggaggtg cacaacgcca agaccaagcc cagagaggag 960
cagtacaaca gcacctacag ggtggtgtcc gtgctgaccg tgctgcacca ggactggctg 1020
aacggcaagg aatacaagtg caaggtctcc aacaaggccc tgccagcccc catcgaaaag 1080
accatcagca aggccaaggg ccagccacgg gagccccagg tgtacaccct gccccccctcc 1140
cgggaggaga tgaccaagaa ccaggtgtcc ctgacctgtc tggtgaaggg cttctacccc 1200
agcgacatcg ccgtggagtg ggagagcaac ggccagcccg agaacaacta caagaccacc 1260
cccccagtgc tggacagcga cggcagcttc ttcctgtaca gcaagctgac cgtggacaag 1320
tccaggtggc agcagggcaa cgtgttcagc tgcagcgtga tgcacgaggc cctgcacaac 1380
cactacaccc agaagagcct gagcctgtcc cccggcaag 1419

<210> SEQ ID NO 15
<211> LENGTH: 705
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15
atgagcgtgc tgacccaggt gctggctctg ctgctgctgt ggctgaccgg caccagatgc 60
gatatcgtgc tgacacagag ccccgccacc ctgagcctga gcccaggcga gagggccacc 120
ctgtcctgca gggccagcca gtttatcagc agcagctacc tgtcctggta tcagcagaag 180
cccggccagg cccctagact gctgatctac ggcagctcct ctcgggccac cggcgtgccc 240
gccaggttca gcggcagcgg ctccggcacc gacttcaccc tgacaatcag cagcctggag 300
cccgaggact tcgccgtgta ctactgccag cagctgtaca gctcacccat gaccttcggc 360
cagggcacca aggtggagat caagcgtacg gtggccgctc ccagcgtgtt catcttcccc 420
cccagcgacg agcagctgaa gagcggcacc gccagcgtgg tgtgcctgct gaacaacttc 480

-continued

| | |
|---|---|
| taccccgggg aggccaaggt gcagtggaag gtggacaacg ccctgcagag cggcaacagc | 540 |
| caggagagcg tcaccgagca ggacagcaag gactccacct acagcctgag cagcaccctg | 600 |
| accctgagca aggccgacta cgagaagcat aaggtgtacg cctgcgaggt gacccaccag | 660 |
| ggcctgtcca gccccgtgac caagagcttc aacaggggcg agtgc | 705 |